(12) United States Patent
Hay et al.

(10) Patent No.: US 6,495,589 B2
(45) Date of Patent: Dec. 17, 2002

(54) SOMATOSTATIN ANTAGONISTS AND AGONISTS THAT ACT AT THE SST SUBTYPE 2 RECEPTOR

(75) Inventors: Bruce A. Hay, East Lyme, CT (US); Bridget M. Cole, Stonington, CT (US); Anthony P. Ricketts, Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/734,789

(22) Filed: Dec. 12, 2000

(65) Prior Publication Data

US 2001/0047030 A1 Nov. 29, 2001

Related U.S. Application Data

(60) Provisional application No. 60/200,319, filed on Apr. 28, 2000.

(51) Int. Cl.⁷ .................... C07D 209/04; A61K 31/40
(52) U.S. Cl. ........................ 514/419; 548/491
(58) Field of Search ............ 548/491; 514/419

(56) References Cited

U.S. PATENT DOCUMENTS

5,270,302 A * 12/1993 Shiosaki et al. ............ 514/18
5,936,089 A 8/1999 Carpino et al. ............ 546/143

FOREIGN PATENT DOCUMENTS

| WO | WO 98/44921 | 10/1998 |
| WO | WO 98/44922 | 10/1998 |
| WO | WO 98/45285 | 10/1998 |
| WO | WO 99/22735 | 5/1999 |
| WO | WO 99/64401 | 12/1999 |
| WO | WO 99/64420 | 12/1999 |

OTHER PUBLICATIONS

Sadaf Farooqu et al., "The Therapeutic Value of Somastatin and Its Analogues" *Pituitary* vol. 2, pp. 79–88 (1999).

Susan P. Rohrer, et al., "Rapid Identification of Subtype–Selective Agonists of the Somatostatin Receptor Through Combinatorial Chemistry" *Science* vol. 282, pp. 737–740; (1998).

Henning Grønbæk, et al. "Potential Role of Octreotide in the Treatment of Diabetes" *Prog Basic Clin Pharmacol. Basel,* vol. 10, pp. 103–128; (1996).

Vicente Martinez, et al., "High Basal Gastric Acid Secretions in Somatostatin Receptor Subtype 2 Knockout Mice"; American *Gastroenterology* (1998) 114 pp. 1125–1132.

Yogesh C. Patel, et al., "Somatostatin Receptors", *TEM*, vol. 8, No. 10, (1997) pp. 398–404.

Lihu Yang, et al., "Synthesis and biological activities of potent peptidomimetics selective for somastotatin receptor subtype 2"; *Proc. Natl. Acad. Sci. USA,* vol. 95, pp. 10836–10841, (1998).

(List continued on next page.)

*Primary Examiner*—Joseph K. McKane
*Assistant Examiner*—Andrea D. Small
(74) *Attorney, Agent, or Firm*—Peter C. Richardson; Paul H. Ginsburg; E. Victor Donahue

(57) ABSTRACT

Compounds according formula (I)

$$A\text{—}G\text{—}Z\text{—}W$$

and pharmaceutically acceptable salts, solvates or hydrates thereof; wherein,

A is $(C_6–C_{10})$aryl, $(C_6–C_{10})$aryl-$SO_2$, $(C_6–C_{10})$aryl-$CH_2$—, $(C_6–C_{10})$arylcarbonyl, $(C_1–C_9)$heteroaryl, $(C_1–C_9)$heteroaryl-$SO_2$—, $(C_1–C_9)$heteroaryl-$CH_2$—; or $(C_1–C_9)$heteroarylcarbonyl;

G is selected from the group consisting of:

(a)

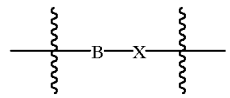

where B is $(C_6–C_{10})$aryl or $(C_1–C_9)$heteroaryl, and X is $CH_2$, $SO_2$, or carbonyl;

(b)

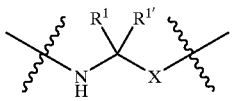

where X is $CH_2$, $SO_2$, or carbonyl; and $R^1$ and $R^{1'}$ are each independently selected from H, CN, $(C_1–C_8)$alkyl-, and phenyl($CH_2$)—, wherein said alkyl and phenyl groups are optionally substituted; and (c)

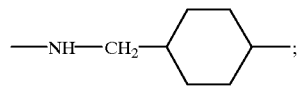

where Z and W are as defined in the present Specification; and pharmaceutical compositions and methods useful to increase secretion of growth hormone(GH) from the anterior pituitary of mammals, including on a sustained release basis.

21 Claims, No Drawings

OTHER PUBLICATIONS

Simon J. Hocart, et al., "Potent Antagonists of Somatostatin: Synthesis and Biology"; *J. Med. Chem.* vol. 41, pp. 1146–1154.

Muhammad Zaki, et al., "Somatostatin Receptor Suptype 2 Mediates Inhibition of Gastrin and Histamine Secretion from Human, Dog and Rat Antrum"; *Gastroenterology* vol. 111, pp. 919–924 (1996).

William R. Baumbach, et al., "A Linear Hexpeptide Somatostatin Antagonist Blocks Somatostatin Activity In Vitro and Influences Growth Hormone Release in Rats" *Molecular Pharmacology,* vol. 54, pp. 864–873 (1998).

Lihu Yang, et al., "Spirol[1H–indene–1,4–piperidine]Derivatives as Potent and Selective Non–Peptide Human Somatostatin Receptor Subtype 2 (SST2) Agonists", *Journal of Medicinal Chemistry,* vol. 41, No. 13, pp. 2175–2179 (1998).

* cited by examiner

SOMATOSTATIN ANTAGONISTS AND AGONISTS THAT ACT AT THE SST SUBTYPE 2 RECEPTOR

The present application claims priority under 35 USC section 119(e) to U.S. Provisional Application No. 60/200,319, filed Apr. 28, 2000, which is incorporated by reference herein as if fully set forth.

FIELD OF THE INVENTION

The present invention provides pharmaceutically active compounds that facilitate secretion of growth hormone (GH) by the anterior pituitary. Growth hormone (also known as somatotropin) acts indirectly to promote skeletal growth in children by stimulating the production of insulin like growth factor-1 from the liver. Growth hormone also stimulates the differentiation of fat cells and chondrocytes (cells that secrete collagen and proteoglycans to form cartilage). In adults, growth hormone is involved in the proper maintenance of connective and muscle tissues.

Growth hormone deficiency may be congenital or acquired. Deficiency in children causes slow skeletal growth that, if not corrected, results in permanent short stature. In older adults, deficiency of growth hormone results in frailty. Additional adult symptoms of GH deficiency may include wrinkled skin and hypoglycemia.

For veterinary application, upregulation of growth hormone is useful to treat frailty in older animals, particularly companion animals. With respect to livestock, upregulation of growth hormone increases growth and performance, even in healthy animals with normal GH levels. Improvements in feed efficiency milk yield, leanness, meat quality and fertility are of note.

Although direct administration of growth hormone may be effective in certain therapeutic applications, it is difficult in practice. Among other issues, since the half-life of growth hormone in the body is very short, direct administration leads to artificially increased levels in the concentration of circulating GH, which then rapidly drop off. Sustained release, such as by a mechanical pump, has not been optimally set to practice.

The concentration of growth hormone circulating in the body depends on the balance of numerous biochemical pathways, including opposing processes. Compared to the direct administration approach, shifting the balance of these pathways indirectly provides a safer, more reproducible method to affect GH secretion on a sustained basis. Under this approach, since the overall regulatory framework remains intact, secretion rates and circulatory concentrations for GH follow a relatively normal pattern, and adverse fluctuations in both secretion rate and circulating GH concentration are avoided. The present invention provides for therapeutic compounds, and their use, to indirectly elevate growth hormone secretion from the pituitary.

Reported Developments

Growth hormone is released from the anterior pituitary in response to stimulation by growth hormone releasing peptide (GHRP), and growth hormone releasing hormone (GHRH), of hypothalmic origin. However, release of growth hormone via these or other mechanisms is inhibited by somatostatin, and thus the process is closely regulated.

Somatostatin (SRIF) is a cyclic peptide hormone of 14 amino acids (there is also a 28 amino acid form) having numerous endocrine functions which, like many hormones, is cleaved from a larger precursor protein. Somatostatin inhibits the pituitary secretion of growth hormone, the pancreatic secretion of glucagon and insulin, and the secretion of gastrin from the gut. Somatostatin also acts as a neurotransmitter/neuromodulator (see S. J. Hocart et al., *J. Med. Chem.*, 41, pp. 1146–1154, 1998 for a general discussion).

The biological effects of somatostatin are apparently all inhibitory in nature, and are elicited upon binding to the surface of a target cell. The receptor is an integral membrane protein (which spans the cell membrane), and is G-protein-coupled. G-protein coupled receptors represent a major class of cell surface receptors. It is believed that upon binding of somatostatin to the receptor, the receptor undergoes a conformational change facilitating its interaction with a G-protein at the cytoplasmic face of the receptor. This facilitates binding or release of GTP/GDP at the G protein, and leads to further activation and signaling events inside the cell. In particular, somatostatin binding at its own G-protein-coupled receptor is negatively coupled to adenylyl cyclase activity, which is necessary for the production of cyclic AMP. Thus, these further signaling events directly oppose mechanisms (for example, as mediated by calcium ions or cyclic AMP) whereby GHRP and GHRH would otherwise trigger extracellular secretion of growth hormone from cytoplasmic storage granules. For a general review thereof, see *The Encyclopedia of Molecular Biology*, J. Kendrew, ed., Blackwell Science, Ltd. 1994, at page 387.

The effects of somatostatin on target cells are mediated by at least 5 classes of receptors (sst1–sst5). Although the receptors may have similar affinity for somatostatin, they are differentially expressed in different tissues, and so positioned, interact, directly or indirectly, with different intracellular signaling components. This tissue specificity of receptor expression accounts in large measure for the different effects of somatostatin in different target cell types. Somatostatin receptors are found, for example, in tissues of the anterior pituitary, other brain tissues, the pancreas, the lung, on lymphocytes, and on mucosa cells of the intestinal tract.

The sst2 type receptor is known to mediate inhibition of growth hormone secretion in the anterior pituitary. This receptor is also reported in 2 forms, proteins sst2A and sst2B, which result from differential splicing of the sst2 gene transcript (M. Vanetti, et al., FEBS Letters, 311, pp.290–294, 1992). The sst2 receptor is also known to mediate inhibition of gastrin and histamine secretion. Additionally, the sst2 receptor is known to mediate inhibition of glucagon release from pancreatic alpha cells.

Although numerous somatostatin agonists have been described (see for example, WO 98/44922, WO 98/45285, and WO 98/44921), the development of useful sst2-linked somatostatin antagonists has lagged behind. Recent reports of such compounds include W. R. Baumbach et al., *Molecular Pharmacology*, 54, pp. 864–873, 1998, and S. J. Hocart et al., *J. Med. Chem.*, 41, pp. 1146–1154, 1998.However, such compounds are short peptides, a class of molecules not often suited for successful use as pharmaceuticals because of their typically short half life in the body.

It would be advantageous to provide antagonists of somatostatin activity, effective at the sst2 type receptor, having superior properties as pharmaceuticals, including bioavailability, stability, and the like. The present invention provides a series of antagonist compounds that specifically interfere with the binding of somatostatin to the sst subtype 2 receptors of cells in the mammalian anterior pituitary, and which have additional valuable properties.

SUMMARY OF THE INVENTION

According to the practice of the present invention, there is provided a compound according to formula (I)

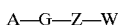
(I)

or a pharmaceutically acceptable salt, solvates or hydrate thereof, wherein group A is $(C_6-C_{10})$aryl, $(C_6-C_{10})$aryl-$SO_2$, $(C_6-C_{10})$aryl-$CH_2$—, $(C_6-C_{10})$arylcarbonyl, $(C_1-C_9)$heteroaryl, $(C_1-C_9)$heteroaryl-$SO_2$—, $(C_1-C_9)$heteroaryl-$CH_2$—; or $(C_1-C_9)$heteroarylcarbonyl;

G is:

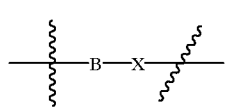
(a)

where B is $(C_6-C_{10})$aryl or $(C_1-C_9)$heteroaryl, and X is $CH_2$, $SO_2$, or carbonyl;

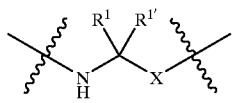
(b)

where X is $CH_2$, $SO_2$, or carbonyl; and $R^1$ and $R^{1'}$ are each independently selected from H, CN, $(C_1-C_8)$alkyl-, and phenyl($CH_2$)—, wherein said alkyl and phenyl groups are optionally substituted; or

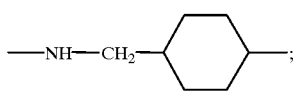
(c)

Z is

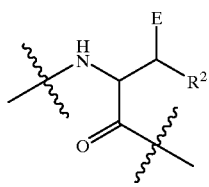

wherein $R^2$ is H, $(C_1-C_8)$alkyl, or is selected from groups A above; and E is selected from groups A above;

W is (a):

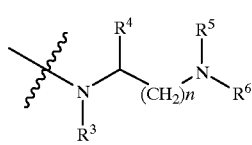
(a)

wherein n is 2 to 5, $R^3$ is selected from H, $(C_1-C_8)$alkyl-, and phenyl($CH_2$)—, wherein said alkyl and phenyl groups are optionally substituted;

$R^6$ is selected from H, $(C_1-C_8)$alkyl-, and phenyl($CH_2$)—, wherein said alkyl and phenyl groups are optionally substituted;

$R^4$ is selected from H, $(C_1-C_8)$alkyl-, and phenyl($CH_2$)—, wherein said alkyl and phenyl groups are optionally substituted; or is

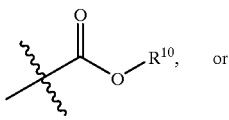
(1)

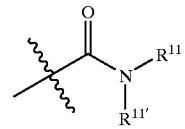
(2)

where groups $R^{10}$, $R^{11}$ and $R^{11'}$ are each, independently, selected from H, $(C_1-C_8)$alkyl-, and phenyl($CH_2$)—, and $R^{10}$ may also be selected from $(C_6-C_{10})$aryl, wherein said alkyl, phenyl or other aryl groups are optionally substituted;

$R^5$ is H, $(C_1-C_8)$alkyl-, and phenyl($CH_2$)—, wherein said alkyl and phenyl groups are optionally substituted, or is

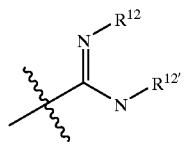

wherein $R^{12}$ and $R^{12'}$ are each independently selected from H, $(C_1-C_8)$alkyl-, and phenyl($CH_2$)—, wherein said alkyl and phenyl groups are optionally substituted; or W is (b)

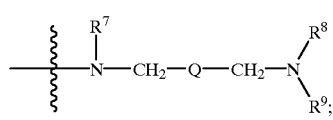
(b)

wherein

Q is selected from the group consisting of $(C_6-C_{10})$aryl, $(C_1-C_9)$heteroaryl, $(C_3-C_{10})$cycloalkyl, and $(C_3-C_{10})$heterocycloalkyl; and $R^7$, $R^8$, and $R^9$ are each independently selected from H, $(C_1-C_8)$alkyl-, and phenyl($CH_2$)—, wherein said alkyl and phenyl groups are optionally substituted.

In a preferred aspect of the invention, there is provided a compound wherein, independently, one or more of groups A, B, E, and Q therein comprise, a $(C_6-C_{10})$aryl group, selected from phenyl and naphthyl.

In a preferred aspect of the invention, there is provided a compound wherein, independently, one or more of groups A, B, E, and Q therein comprise, a $(C_1-C_9)$heteroaryl group, selected from furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-

[1]pyrindinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, and benzoxazinyl.

In a preferred aspect of the invention, there is provided a compound wherein group Q therein is selected from (a) a $(C_6-C_{10})$aryl group, selected from phenyl and naphthyl;

(b) a $(C_1-C_9)$heteroaryl group, selected from furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, and benzoxazinyl;

(c) a $(C_3-C_{10})$cycloalkyl group, selected from cyclopropyl, cyclobutyl, cyclopentyl, cyclohexyl, cycloheptyl, cyclopropenyl, cyclobutenyl, cyclopentenyl, cyclohexenyl, cycloheptenyl, 1,3-cyclobutadienyl, 1,3-cyclopentadienyl, 1,3-cyclohexadienyl, 1,4-cyclohexadienyl, 1,3-cycloheptadienyl, 1,4-cycloheptadienyl, 1,3,5-cycloheptatrienyl, bicyclo[3.2.1]octane, bicyclo [2.2.1] heptane and the norborn-2-ene unsaturated form thereof; and (d) a $(C_3-C_{10})$heterocycloalkyl group, selected from pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, and chromanyl.

In a highly preferred embodiment of the invention, there is provided a compound wherein the Z group thereof has the stereospecificity

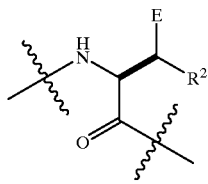

In further examples of this embodiment, the Z group defines an L-amino acid selected from the group consisting of L-tryptophanyl-, L-histidinyl-, L-3-methylhistidinyl-, L-phenylalaninyl-, L-diphenylalaninyl-, L-3-fluorophenylalaninyl-, L-2-fluorophenylalaninyl-, L-4-fluorophenylalaninyl-, and L-tyrosinyl-, and is most preferably L-tryptophanyl-.

In a further preferred embodiment of the invention, there is provided a compound wherein the Z group thereof has the stereospecificity

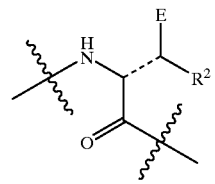

and thus the Z group defines an D-amino acid which is preferably D-tryptophanyl.

In a further highly preferred embodiment of the invention, there is provided a compound wherein the W group thereof has an absolute stereospecific configuration at the indicated position which corresponds to the that of the α-carbon of L-amino acids.

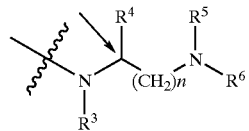

It is further preferred that the W group define an L-lysine group or a $(C_1-C_8)$alkyl ester thereof, or an L-arginine group or a $(C_1-C_8)$alkyl ester thereof, most preferably an $(C_1-C_8)$ alkyl ester of L-lysine. Additionally, the W group can define an L-diaminopimelic, L-canavanine, L-ornithine, L-2,4-diaminobutyric, L-5-hydroxylysine, L-epsilon-N-methyllysine, L-histidine, or L-3-methylhistidine group.

Accordingly, preferred compounds of the invention include:

6-Amino-2-[2-[(biphenyl-4-ylmethyl)-amino]-3-(1H-indol-3-yl)-propionylamino]-hexanoic acid methyl ester;

2-{3-(3-Fluoro-phenyl)-2-[2-(toluene-4-sulfonylamino)-acetylamino]-propionylamino}-5-guanidino-pentanoic acid methyl ester;

6-Amino-2-[2-[(biphenyl-4-carbonyl)-amino]-3-(1H-indol-3-yl)-propionylamino]-hexanoic acid methyl ester;

2-{2-[(Biphenyl-4-carbonyl)-amino]-3,3-diphenyl-propionylamino}-5-guanidino-pentanoic acid methyl ester;

6-Amino-2-[2-[(biphenyl-4-carbonyl)-amino]-3-(1H-indol-3-yl)-propionylamino]-hexanoic acid tert-butyl ester;

6-Amino-2-[2-(2-benzenesulfonylamino-2-methyl-propionylamino)-3-(1H-indol-3-yl)-propionylamino]-hexanoic acid tert-butyl ester; and 6-Amino-2-[2-[(biphenyl-4-carbonyl)-amino]-3-(1H-indol-3-yl)-propionylamino]-hexanoic acid tert-butyl ester.

Additional compounds of the invention include:

2-{3-(3-Fluoro-phenyl)-2-[2-(toluene-4-sulfonylamino)-acetylamino]-propionylaminol}-5-guanidino-pentanoic acid tert-butyl ester;

2-{3-(4-Fluoro-phenyl)-2-[2-(toluene-4-sulfonylamino)-acetylamino]-propionylaminol}-5-guanidino-pentanoic acid methyl ester;

2-{3-(3-Fluoro-phenyl)-2-[2-(toluene-4-sulfonylamino)-2-methylpropionylamino]-propionylamino}-5-guanidino-pentanoic acid methyl ester;

6-Amino-2-[2-[(biphenyl-4-carbonyl)-amino]-3-(1H-indol-3-yl)-propionylamino]-hexanoic acid tert-butyl ester;

6-Amino-2-[2-[(biphenyl-4-carbonyl)-amino]-2-methyl-3-(1H-indol-3-yl)-propionylamino]-hexanoic acid tert-butyl ester;

N-(3-aminomethyl-cyclohexylmethyl)-3-(1H-indol-3-yl)-2-(2-benzenesulfonylamino-2-methyl-propionylamino)-propionamide; and N-(4-aminomethyl-pyrid-2-ylmethyl)-3-(1H-indol-3-yl)-2-[(biphenyl-4-carbonyl)-amino]-propionamide.

In further compounds of the invention, $R^1$ or $R^{1'}$ is $(C_1-C_8)$alkyl- or phenyl$(CH_2)$— and said alkyl or phenyl group is optionally substituted by one or more halo or trifluoro$(C_1-C_8)$alkyl groups.

In further compounds of the invention, $R^2$ is $(C_1-C_8)$ alkyl-, optionally substituted by one or more halo or trifluoroalkyl groups, most preferably $(C_1-C_3)$alkyl-, optionally substituted by one or more halo or trifluoro$(C_1-C_8)$alkyl groups.

In further compounds of the invention, one or more of $R^3$, $R^4$, $R^5$, and $R^6$ is $(C_1-C_8)$alkyl- or phenyl$(CH_2)$—, and said alkyl or phenyl group is optionally substituted by one or more halo or trifluoro$(C_1-C_8)$alkyl groups.

In further compounds of the invention, one or more of $R^7$, $R^8$, and $R^9$ is $(C_1-C_8)$alkyl- or phenyl$(CH_2)$—, and said alkyl or phenyl group is optionally substituted by one or more halo or trifluoro$(C_1-C_8)$alkyl groups.

In further compounds of the invention, one or more of $R^{10}$, $R^{11}$, $R^{11'}$, $R^{12}$ and $R^{12'}$ is $(C_1-C_8)$alkyl- or phenyl $(CH_2)$—, and said alkyl or phenyl group is optionally substituted by one or more halo or trifluoro$(C_1-C_8)$alkyl groups.

With respect to trifluoro$(C_1-C_8)$alkyl substituent groups, all as aforementioned, the prefered group is trifluoromethyl.

The compound of formula (I) may have chiral centers and therefore exist in different enantiomeric forms. This invention relates to all optical isomers, tautomers and stereoisomers of the compounds of formula (I), and mixtures thereof, although as will be described below in greater detail, certain isomeric structures are preferred.

The present invention also relates to the pharmaceutically acceptable acid addition salts of compounds of the formula (I). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

With respect to the relatively limited number of compounds that so permit, the invention also relates to base addition salts of formula (I). The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g, calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labelled compounds, which are identical to those recited in Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula (I) of this invention and prodrugs thereof can generally be prepared by carrying out the procedures disclosed in the Schemes and/or in the Examples and Preparations below, by substituting a readily available isotopically labelled reagent for a non-isotopically labelled reagent.

The present invention also relates to a pharmaceutical composition for increasing growth hormone secretion in a mammal, including a human, comprising an effective amount of a compound according to formula 1, and a pharmaceutical carrier. The present invention also relates to a pharmaceutical composition for increasing gastrin secretion or glucagon secretion in a mammal, comprising an effective amount of a compound according to formula 1, and a pharmaceutical carrier.

The present invention also relates to a pharmaceutical composition for the treatment of diseases characterized by decreased levels of growth hormone, glucagon, or gastrin in a mammal, including a human, comprising an amount of a compound of formula (I) effective in such treatments and a pharmaceutically acceptable carrier. The present invention also relates to a pharmaceutical composition for the treatment of diseases in a mammal, including a human, wherein treatment can be effected by inhibiting the binding of somatostatin to the sst2-type receptor therefor, comprising an effective amount of a compound according to formula 1, and a pharmaceutical carrier.

The present invention relates to a method for treating growth hormone deficiency in a mammal, including a human. The present invention also relates to elevating the level of growth hormone in a mammal, including a human, wherein this is beneficial to the mammal nothwithstanding that the natural levels of growth hormone present in the mammal are within the normal range. In the practice of said method, there is administered a phamaceutical composition of the invention comprising a compound according to formula (1), and a pharmceutical carrier.

Similarly, the methods of the invention provide for increasing gastrin secretion or glucagon secretion in a mammmal, including a human, where this is medically appropriate. For example, gastrin is involved in protection of gastric mucosa against damage by chemical substances, e.g. alcohol (S. J. Konturek et al., *European Journal of Pharmacology*, 278(3), pp. 203–212, 1995). Glucagon is a counter-regulatory hormone that is used to treat hypoglycemia, and causes positive inotropic and chronotropic effects without the need for beta-1 adrenoceptor stimulation. It also can be used to correct beta-blocker, verapamil and imipramine overdose, and is used as adjunctive therapy in shock situations, for heart failure, and in treating post-countershock asystole (see C. M. White, *Journal of Clinical Pharmacology,*. 39(5), pp. 442–447, 1999)

In preferred examples of the invention, there are provided methods for treating a human for one or more symptoms of insufficient growth hormone secretion, or one or more conditions that may occur therewith and be exacerbated thereby, wherein said condition is selected from frailty, hypoglycemia, wrinkled skin, slow skeletal growth, reduced immune function, reduced organ functon, fertility disorders, bone disease, AIDS-related complex, cachexia, cardiac failure, ischemic heart disease, colon disease, metabolic disorders, renal failure, muscular dystrophy, and Turners syndrome, comprising administering an effective amount of a pharmaceutical composition as aforementioned.

In a further preferred example of the invention, there is provided a method for treating a non-human mammal to enhance the growth and performance thereof, comprising administering an effective amount of a pharmaceutical composition as aforementioned. Enhancement of growth and performance includes, for example, increased feed efficiency, improved milk yield or fertility, and increased leanness.

A highly preferred example of the invention provides a method whereinby secretion of growth hormone, gastrin, or glucagon can be increased on a sustained basis in a mammal, including a human, in need thereof, comprising adminstering a dose of a pharmaceutical composition as aforementioned. According to this example of the invention, physiologically adverse consequences of artificial fluctuations in the circulating (or locally needed) concentrations of these hormones can be avoided.

Although the pharmaceutical compositions and methods of the invention are described primarily in terms of use with humans, and non-human mammals, the skilled practitioner will immediately appreciate that the invention, in many of its aspects, may be usefully practiced with respect to birds, such as chickens and turkeys, and also fishes.

Definitions

In connection with the practice of the invention, the following definitions will generally apply.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "alkyl", as used herein, unless otherwise indicated, includes saturated monovalent hydrocarbon radicals having straight, branched or cyclic moieties or combinations thereof. Similarly, the terms "alkenyl" and "alknyl" define hydrocarbon radicals having straight, branched or cyclic moieties wherein at least one double bond, or at least one triple bond, respectively, is present. Such definitions also apply when the alkyl, alkenyl or alkynyl group is present within another group, such as alkoxy or alkylamine.

The term "alkoxy", as used herein, includes O-alkyl groups wherein "alkyl" is as defined above.

The term "halo", as used herein, unless otherwise indicated, includes fluoro, chloro, bromo or iodo.

An "aryl" group as used herein, unless otherwise indicated, includes an organic radical derived from a monocyclic or bicylic ($C_6$–$C_{10}$) aromatic hydrocarbon compound by removal of a hydrogen radical from a ring carbon of the aryl compound. An aryl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative aryl groups are phenyl and naphthyl.

A "heteroaryl" group as used herein, unless otherwise indicated, includes an organic radical derived from a monocyclic or bicyclic ($C_1$–$C_9$) aromatic heterocyclic compound by removal of a hydrogen radical from a ring atom of the heteroaryl compound, said ring atom being uncharged in said compound. A heteroaryl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative heteroaryl groups include furyl, thienyl, thiazolyl, pyrazolyl, isothiazolyl, oxazolyl, isoxazolyl, pyrrolyl, triazolyi, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6, 7, 8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, and benzoxazinyl; and the like.

A "cycloalkyl" group as used herein, unless otherwise indicated, includes an organic radical derived from a monocyclic ($C_3$–$C_{10}$)cycloalkyl compound, by removal of a hydrogen radical from a ring carbon of the cycloalkyl compound. A cycloalkyl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative cycloalkyl groups include cyclopropyl, cyclobutyl, cyclopentyl, cyclohexyl, cycloheptyl, cyclopropenyl, cyclobutenyl, cyclopentenyl, cyclohexenyl, cycloheptenyl, 1,3-cyclobutadienyl, 1,3-cyclopentadienyl, 1,3-cyclohexadienyl, 1,4-cyclohexadienyl, 1,3-cycloheptadienyl, 1,4-cycloheptadienyl, 1,3,5-cycloheptatrienyl, bicyclo[3.2.1]octane, bicyclo [2.2.1] heptane, and the norborn-2-ene unsaturated form thereof.

A "heterocycloalkyl" group as used herein, unless otherwise indicated, includes an organic radical derived from a monocyclic ($C_3$–$C_{10}$)heterocycloalkyl compound by removal of a hydrogen radical from a ring atom of the heterocycloalkyl compound, said ring atom being uncharged in said compound. (fix) A heterocycloalkyl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative heterocycloalkyl groups include pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, and chromanyl.

In connection with the terms "aryl" group, "heteroaryl" group, "cycloalkyl" group and "heterocycloalkyl" group, as herein defined, the term "optionally substituted" means that one or more chemically and pharmaceutically acceptable functional groups may be bonded thereto. Such a group contributes properties useful to production, storage, or use of the inventive compounds as pharmaceuticals, or at least does not substantially negate their pharmacological activity. Such suitable substituents may be determined by those skilled in the art. Illustrative examples of suitable substituents include, but are not limited to, hydroxy, halo, amino, trifluoromethyl, carboxy, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$acylamino-, cyano, nitro, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl$(C_1-C_6)$alkyl-, nitro$(C_1-C_6)$alkyl-, $(C_1-C_3)$alkyl(difluoromethylene)$(C_1-C_3)$alkyl-, $(C_1-C_6)$acylamino$(C_1-C_6)$alkyl-, $(C_1-C_6)$alkoxy$(C_1-C_6)$acylamino-, amino$(C_1-C_6)$acyl-, amino$(C_1-C_6)$acyl$(C_1-C_6)$alkyl-, $(C_1-C_6)$alkylamino$(C_1-C_6)$acyl-, $((C_1-C_6)$alkyl$)_2$amino$(C_1-C_6)$acyl-, $(C_3-C_{10})$cycloalkyl$(C_1-C_6)$alkyl-, $(C_1-C_6)$acyloxy$(C_1-C_6)$alkyl-, $(C_2-C_6)$alkoxy$(C_1-C_6)$alkyl-, piperazinyl$(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkylsulfinyl$(C_1-C_6)$alkyl- $(C_6-C_{10})$arylsulfinyl$(C_1-C_6)$alkyl-, $(C_1-C_6)$alkylsulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6)$alkyl-, $(C_1-C_6)$alkyl(difluoromethylene)-, $(C_1-C_3)$alkyl(difluoromethylene)$(C_1-C_3)$alkyl-, $(C_1-C_6)$alkoxy$(C_1-C_6)$acyl-, $(C_1-C_6)$alkylamino$(C_1-C_6)$acyl-, $((C_1-C_6)$alkyl$)_2$amino$(C_1-C_6)$acyl-, $(C_6-C_{10})$aryl-, $(C_5-C_9)$heteroaryl-, $(C_6-C_{10})$aryl$(C_1-C_6)$alkyl-, $(C_2-C_9)$heteroayl$(C_1-C_6)$alkyl-, $(C_6-C_{10})$aryl$(C_6-C_{10})$aryl-, $(C_6-C_{10})$aryl$(C_6-C_{10})$aryl$(C_1-C_6)$alkyl- $(C_3-C_{10})$cycloalkyl-, $(C_3-C_6)$cycloalkyl$(C_1-C_6)$alkyl-, $(C_3-C_{10})$heterocycloalkyl-, $(C_3-C_{10})$heterocycloalkyl$(C_1-C_6)$alkyl-, hydroxy$(C_2-C_6)$alkyl-, $(C_1-C_6)$acyloxy$(C_2-C_6)$alkyl-, $(C_1-C_6)$alkoxy$(C_2-C_6)$alkyl-, piperazinyl$(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkylsulfinyl$(C_1-C_6)$alkyl-, $(C_6-C_{10})$arylsulfinyl$(C_1-C_6)$alkyl-, $(C_1-C_6)$alkylsulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6)$alkyl-, and $((C_1-C_6)$alkyl$)_2$amino$(C_1-C_6)$alkyl.

Further aspects of the invention are described in accord with the Detailed Description of the invention which follows directly.

DETAILED DESCRIPTION OF THE INVENTION

According to the practice of the present invention, the secretion of growth hormone from cells (such as those of the anterior pituitary) is facilitated by inhibiting the somatostatin-induced (and G-protein coupled) mechanisms that naturally oppose both calcium ion and cyclic AMP-mediated signals that otherwise trigger fusion with the cell membrane of cytoplasmic granule structures that contain growth hormone, and the subsequent release (secretion) of GH.

The present invention provides an effective approach to the treatment of frailty in older persons, which may be caused, in whole or part, by insufficient levels of growth hormone (GH), or impairment of any of several downstream physiological effects normally associated with growth hormone secretion. It is generally recognized that GH is important to the maintenance of connective and muscle tissue in adults, and may help, to some extent, to increase muscle mass. Thus growth hormone may be used to assist elderly patients even when growth hormone levels per se are not the cause of, for example, weakness, or attrition of muscle and connective tissues. The practice of the invention benefits other patients, such as children, when it can be demonstrated that secretion of growth hormone is inadequate, but is subject to enhancement. Deficiency in GH secretion, or resultant GH activity, may arise in several ways. For example, the gene sequence that encodes GH may be expressed in the nucleus at subnormal levels, processing of resultant RNA transcript or nascent polypeptide may be defective, or fusion of cytoplasmic GH storage granules with the cell membrane (with resultant release of GH) may be defective. Additionally, the patient may possess an allele of the GH gene that encodes a mutant protein having less biological activity. Alternatively, there may be an underlying deficiency of GHRH, or a defect in the GHRH receptor, or defects in the the GHRP receptor or deficiency of its endogenous ligand, or in respective signalling mechanisms. Additionally, there may be an excess of somatostatin. In all such cases, the resultant physiological deficiency can be treated by administration of the pharmaceutical compounds of the invention.

In a further aspect of the invention, the performance and growth rate of non-human mammals, such as livestock, is enhanced by appropriate administration of the compounds disclosed herein. Additionally, companion animals, and particularly older companion animals also benefit upon administration of the present compounds.

Although the compounds of the present invention act to indirectly facilitate release of mature growth hormone from the cytoplasmic storage granules of cells, additional therapeutic substances are known that can directly enhance such secretion, and further, can indirectly enhance production of growth hormone by via enhanced expression of GH-encoding DNA in the cell nucleus. In this regard, both growth hormone releasing peptide (GHRP) and growth hormone releasing hormone (also known as growth hormone releasing factor, GHRH/GRF) which act to release GH from cytoplasmic storage granules have been mentioned. Since the release of GH from such granules has been implicated as a signal triggering production of additional GH protein in the cells, it is expected that GH levels may be properly maintained in patients using a "push-pull" approach.

Accordingly, a further preferred example of the invention provides for the co-administration of the somatostain-antagonist compounds of the present invention and GHRP or GHRH, or other substances of like effects. Medical treatment with GHRP (or GHRH) alone is described in the following representative publications: M. Thorner et al., *Journal Of Clinical Endocrinology And Metabolism*, 81(3), pp. 1189–1196, 1996; S. G. Celia et al., *Peptides*, 16(1), pp. 81–86, 1995; M. A. Bach et al., *Journal Of The American Geriatrics Society*, 44(9), S10, 1996; and J. A. Aloi et al., *Journal Of Clinical Endocrinology And Metabolism*, 79(4), pp. 943–949, 1994.

Finally, since growth hormone is very labile, and its half-life in the body is very short, it is difficult to provide a safe dosing program for direct administration of growth hormone itself, which avoids wide swings in circulating levels of the hormone. Current sustained release technologies for direct administration of growth hormone can be improved upon. In this regard, the practice of the present invention is particularly valuable to the clinician, since by only indirectly raising GH levels, the hormone's release profile remains, at least in part, under the control of the body's own regulatory feedback systems, and fluctuations in the levels of circulating GH are damped over time.

In the preferred practice of the invention, compounds show selectivity for the sst2 receptor compared with other receptor subtypes, for example sst1, sst3, sst4 and sst5. This selectivity minimizes the chance that other molecular biological or biochemical pathways will be adversely affected while growth hormone secretion is being upregulated. Most preferably, the affinity of a compound for the sst2 type receptor should be at least about 10 times greater than for receptors of the other sst-subtypes.

It should be noted that the compounds of the invention may work by more than one mechanism, including those unrelated to interaction at an sst-type receptor, and the utility of the present compounds in the practice of the invention, including for use in treating other disease states not particularly mentioned herein, is not limited by any particular theory as desrcibed herein or by those theories that is generally recognized by those skilled in the art.

Additionally, the compounds of the present invention may interact beneficially with sst-type receptors other than sst2, and may provide therapeutic benefits by acting as somatostatin agonists, rather than antagonists, at sst2 or other sst-type receptors. Various types of somatostain agonists are well known in the art, and the capacity of a compound of the present invention to act as an agonist, an antagonist, or as either, depending on physiological circumstances, can be predicted from the assays which are known in the art and/or described below. For example, measurement of cyclic-AMP, growth hormone release, microphysiometry responses, cell proliferation or protein kinase activity can be measured in cultured pituitary cells, cell lines or other cells such as neuroblastoma cells that express somatostatin receptors, and cells transfected with recombinant somatostatin receptors-including transfected yeast cells. (Y. C. Patel et al., *Biochemical & Biophysical Research Communications*, 198(2), pp. 605–612, 1994; M. G. Cattaneo et al., *FEBS Letters*, 397(2–3), pp. 164–168, 1996; J. A. Koenig et al., *British Journal of Pharmacology*, 120(1), pp. 45–51, 1997; D. Djordjijevic et al., *Endocrinology*, 139(5), pp. 2272–2277, 1998; W. R. Baumbach et al., *Molecular Pharmacology*, 54(5), pp. 864–73, 1998.

Generally, somatostatin or agonists thereof demonstrate inhibitory activity, hence a stimulus is first applied (e.g. forskolin for cyclic-AMP) and the inhibitory effect of somatostatin observed. Antagonists reverse the inhibitory effects of somatostatin.

Somatostatin agonists are recognized as useful therapeutics in the treatment of diabetes, for example, see H. Grønbæck et al., *Prog. Basic Clin Pharmacol.* (Basel), 10, pp. 103–128, 1996. Somatostatin agonists are also recognized (see WO 98/44922) as useful therapeutics in the treatment of, for example, diabetic retinopathy, acromegaly, rheumatoid arthritis, neuropathic and visceral pain, irritable bowel syndrome, Crohn's disease, and are useful to inhibit cell proliferation associated with cancer, and to prevent restenosis following angioplasty.

Additionally, it has been determined that compounds having affinity for sst2 receptors also have affinity for receptors such as mcr4 and MCH. sst2 receptors and MCH receptors are also >50% homologous. Thus the compounds of the present invention may also be used to treat medical conditions mediated through such other receptors.

As aforementioned. the compounds of this invention include all conformational isomers (e.g., cis and trans isomers, whether or not involving double bonds), tautomers, and all optical isomers of compounds of the formula I (e.g., enantiomers and diastereomers), as well as racemic, diastereomeric and other mixtures of all such isomers. With respect to the design of the compounds of the invention, particular features involving conformational and optical isomerism are of note.

In the below structure of a compound of formula (I), it is preferred that the Z group thereof have the following stereospecificity

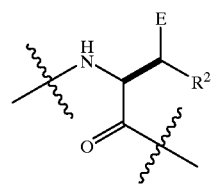

Thus, the Z group defines an L-amino acid, preferably selected from the group consisting of L-tryptophanyl, L-histidinyl, L-3-methylhistidinyl, L-phenylalaninyl-, L-diphenylalaninyl-, L-3-fluorophenylalaninyl-, L-2-fluorophenylalaninyl-, L-4-fluorophenylalaninyl-, and L-tyrosinyl-, and which is most preferably, L-tryptophanyl.

It is less preferred that group Z have the following stereospecificity

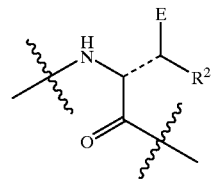

wherein the Z group defines a D-amino acid; however, in this case, use of D-tryptophanyl- is highly preferred.

In the below structural component of a compound of formula (I), it is preferred that the W group thereof have a stereospecificity at the indicated position (which corresponds to the α-carbon of an amino acids), such that L-amino acids, or other structures having the same absolute stereospecificity, are defined.

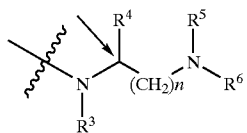

In preferred examples, the W group defines an L-lysine group or a $(C_1-C_8)$alkyl ester thereof, or an L-arginine group or a $(C_1-C_8)$alkyl ester thereof, and in a highly preferred example there is defined a $(C_1-C_8)$alkyl ester of L-lysine. Additionally, the W group can define an L-diaminopimelic, L-canavanine, L-ornithine, L-2,4-diaminobutyric, L-5-hydroxylysine, L-epsilon-N-methyllysine, L-histidine, or L-3-methylhistidine group.

Additionally, L-lysine is preferably selected to provide the "W" component, when Trp derivatives (whether L or R) are used to provide the "Z" component.

L-Arginine is preferably selected to provide the "W" component when Phe (or a derivative thereof such as 2-fluorophenylalaninyl-, 3-fluorophenylalaninyl-, 4-fluorophenylalaninyl- or diphenylalaninyl-) is used to provide the "Z" component. In this case, the stereochemistry provided within Phe, or a derivative thereof, should correspond to that of L-amino acids, if possible.

Additionally, many of the groups of the present compounds may be optionally substituted. As aforementioned, such substituents contribute properties useful to production, storage, or use of the inventive compounds as pharmaceuticals, or at least does not substantially negate their pharmacological activity. It will be appreciated that selection of optional substituents is further guided by principles recognized in the art, and/or is capable of validation through the use of the assays described in the present specification.

Pharmaceutical Formulations

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared, for example, by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

In a preferred example of the invention, the compounds of the present invention may be formulated with additional pharmaceutically active substances that directly or indirectly facilitate production and storage in cells of additional growth hormone, or precursor polypeptides thereof, or release of GH. Such additional substances include growth hormone releasing peptide (GHRP), growth hormone releasing hormone (GHRH), pituitary adenylate cyclase activating polypeptide (PACAP), dopaminergic agonists (e.g. bromocriptine), beta-adrenergic agonists (e.g. isoproterenol) and alpha 1-adrenergic agonists (e.g. methoxamine). For background information see E. O Soyoola et al., Proceedings of the *Society for Experimental Biology & Medicine*, 207(1), pp. 26–33, 1994; V. Locatelli et al., *Pediatric Research*, 36(2), pp. 169–74, 1994; and B. Velkeniers et al., *Journal of Endocrinology*, 143(1), pp. 1–11, 1994.

Equivalently, the additional pharmaceutically active substances may be provided as a separate formulation which is co-administered, or administered at some other timepoint(s) in the course of treatment.

This invention also encompasses pharmaceutical compositions containing prodrugs of compounds of the formula I. This invention also encompasses methods of treating or preventing disorders that can be treated or prevented by decreasing the levels of somatostatin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will also appreciate that when using the compounds of the invention in the treatment of a specific disease, that the compounds of the invention may be combined with various existing therapeutic agents used for that disease, or for other metabolically related or unrelated disease states that may occur simultaneously. As aforementioned, the additional pharmaceutically active substances may be provided as a separate formulation which is co-administered, or administered at some other timepoint(s) in the course of treatment.

The compounds of the invention can also be used in combination with existing therapeutic agents such as the above mentioned growth hormone secretagogues for the treatment of growth hormone deficiency.

For the treatment of growth hormone deficiency, the compounds of the invention may be combined with agents such as recombinant growth hormone which is marketed by Genentech and licensees (Neutropin, Genotropin and Protropin), Bio-Technology General and licensees (Zomacton, Growject, Elvetium and SciTropin), Novo Nordisk (Norditropin), LG Chem (Eutropin), Ares Serono (Saizen and Serostim), Eli Lilly Co (Humatrope), Monsanto (Posilac brand of bovine growth hormone) and Alpharma (Reporcin brand of swine growth hormone).

The compounds of the invention can also be used in combination with existing therapeutic agents such as Geref (sermorelin, GHRH) from Serono Laboratories Inc.

The compounds of the invention can also be used in combination with existing therapeutic agents such as anabolic steroids, e.g. androisoxazol androstanolone (DHT, dihydrotestosterone, Stanolone, Anabolex, Andractrim), bolandiol, bolasterone, bolazin, boldenone (Equipoise), calusterone, clostebol (chlortestosterone, Steranabol, Alfa Trofodermin, Dermanabol, Trofodermin, Trofoseptine), danazol (Cyclomen, Danocrine), dehydrochlormethyltestosterone (turinabol, Oral-turinabol), drostanolone (dromostanolone, Drolban, Masterid, Masteril, Masteron, Metormon, Premastril), estradiol, ethylestrenol, fluoxymesterone (Halotestin, Ora-Testryl, Android-F), formebolone, furazabol (Miotolon), mestanolone, mesterolone (Proviron, Pluriviron), methandienone (methandrostenolone, Metaboline), methandriol, methenolone (Primobolan), methyltestosterone (Methandren, Premarin with methyltestosterone, Android, Oreton, Testred, Methyltestosterone tabs, Geri-Bons, Geri-tabs, Dermonal), mibolerone (Cheque), nandrolone (Deca-Durabolin, Durabolin, Nandrabolin, Anabolin, Androlone, Hybolin, Nandrobolic), norclostebol, norethandrolone (Nilevar), oxabolone, oxandrolone (Anavar), oxymesterone (Oranabol), oxymetholone (Anapolon 50, Androyd, Anadrol, Anasteron, Dynasten, Oxitosona, Plenastril, Synasteron, Zenalosyn), penmesterol, prasterone, quinbolone, stanozolol (Winstrol, Winstrol-V, Stromba, Strombaject), stenbolone, testosterone (Malogen, Delatestryl, Malogen, Neo-pause, PMS-testosterone Enanthate, Andriol, Duogex, Neo-Pause, Climacteron, Orchisterone-P, Oreton, Anadiol, Anatest, Testos-100, Heifer-aid, Synovex-H), tibolone, trenbolone (Parabolan, Finaject) or zeranol.

The compounds of the invention can also be used in combination with existing therapeutic agents such as Somazon (mecasermin, recombinant insulin-like growth factor I) from Fujisawa.

For the treatment of older patients with osteoporosis, suitable agents to be used in combination with the compounds of the invention include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with osteoporosis agents such as lasofoxifene, raloxifene, droloxifene or fosomax and immunosuppressant agents such as FK-506 and rapamycin.

The compounds of the present invention may also be used in combination with immunostimulant agents for the treatment of reduced immune function.

The compounds of the present invention may also be used in combination with fertility agents such as human menopausal gonadotropin, chorionic gonadotropin, follicle stimulating hormone, nafarelin, triptorelin, cetrorelix, and ganirelix for the treatment of infertility.

The compounds of the present invention may also be used in combination with AIDS therapies for the treatment of AIDS-related complex.

The compounds of the present invention may also be used in combination with anti-tumor necrosis factor agents such as infliximab (TNF monoclonal antibody) or etanercept (soluble TNF receptor) for the treatment of cachexia.

The compounds of the present invention may also be used in combination with potassium channel blockers, beta-blockers, anticoagulants or vasodilators for the treatment of heart disease.

The compounds of the present invention may also be used in combination with angiotensin II (ATII) antagonists or erythropoietin for the treatment of renal failure.

For administration to livestock, the compounds of the invention may also be used in combination with feed additives such as antibiotics (e.g. monensin, lasalocid, salinomycin, semduramicin, narasin, maduramicin, virginiamycin, polymixin, efrotomycin, avoparcin, lincomycin, bacitracin, bambermycins, novobiocin, erythromycin, oleandomycin, streptomycin, tylosin, penicillin, tetracycline, oxytetracycline, chlortetracycline, carbadox, olaquindox, neomycin moenomycin avilamycin and flavophospholipol), repartitioning agents, beta-agonists (e.g. Paylean, ractopamine, from Elanco), and also amiterol, bambuterol, bitolterol, broxaterol, buphenine, carbuterol, cimaterol, clenbuterol, clorprenaline, colterol, denopamine, dioxethedrine, dioxifedrine, dobutamine, dopexamine, doxaminol, etanterol, fenoterol, flerobuterol, formoterol, hexoprenaline, ibuterol, imoxiterol, isoetarine, isoxsuprine, levisoprenaline, mabuterol, mesuprine, metaterol, methoxyphenamine, nardeterol, orciprenaline, picumeterol, pirbuterol, prenalterol, procaterol, protokylol, quinprenaline, rimiterol, ritodrine, salbutamol, salmeterol, terbutaline, tretoquinol, tulobuterol, xamoterol and zilpaterol.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets, chewable tablets, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner, or blended with petfood or animal feed, or as a pre-mix for blending with animal feed.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human is 0.1 to 100 mg of the active ingredient per unit dose which could be administered, for example, 1 to 4 times per day.

Aerosol formulations for treatment of the conditions referred to above in the average adult human are preferably arranged so that each metered dose or "puff" of aerosol contains 20 µg to 1000 µg of the compound of the invention. The overall daily dose with an aerosol will be within the range 0.1 mg to 100 mg. Administration may be several times daily, for example 2, 3, 4 or 8 times, giving for example, 1, 2 or 3 doses each time.

Injected doses are preferably administered from about once a month, up to about 1 to 4 times per day, at an individual dosing of 0.01–1 mg/kg (of active ingredient) and may be intramuscular, intravenous, or subcutaneous, for example.

As is well recognized, the precise dose, and method and timing of administration thereof, are capable of determination by those skilled in the art, and depend upon numerous factors including the activity of the therapeutic compound, the properties of the formulation thereof, the nature and location of the target tissue, and the particulars of the disease state as it exists in a particular patient. Additionally, when the compounds of the present invention are administered to a patient with additional pharmaceutically active substances, one or more pharmaceutical compositions may be used to deliver all of the active agents, which may be administered together, or at different times, as determined by those skilled in the pharmaceutical or medical arts.

The following reaction schemes illustrate preparation of compounds of the present invention. It will be appreciated that the groups represented by letters ("R" groups, and the like) in the Schemes do not always correspond with similarly defined component groups of the formula (I) compounds themselves, since certain functionalities of the reactants are modified when the products are formed. Thus, to facilitate presentation of the schemes, $R^1$ and $R^{1'}$, as referred to below, correspond to $R^1$ and $R^{1'}$ as used throughout the Specification in defining the compounds of formula (I), whereas $Ar_1$, $Ar_2$, $Ar_3$, and $R_2$ represent structures that overlap with those as elsewhere defined, as is readily apparent upon inspection. For example, $Ar_1$, $Ar_2$, and $Ar_3$ do not correspond to "A", but rather represent any $(C_6-C_{10})$aryl or $(C_1-C_9)$heteroaryl group as defined herein. $R_2$ typically represents an alkyl group, whether primary, secondary, or tertiary, but can also be aryl or benzyl.

Scheme I

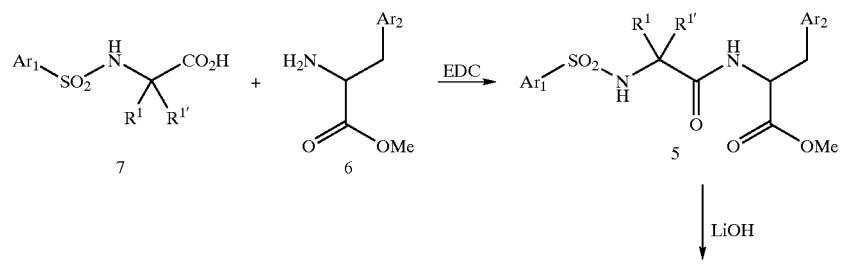

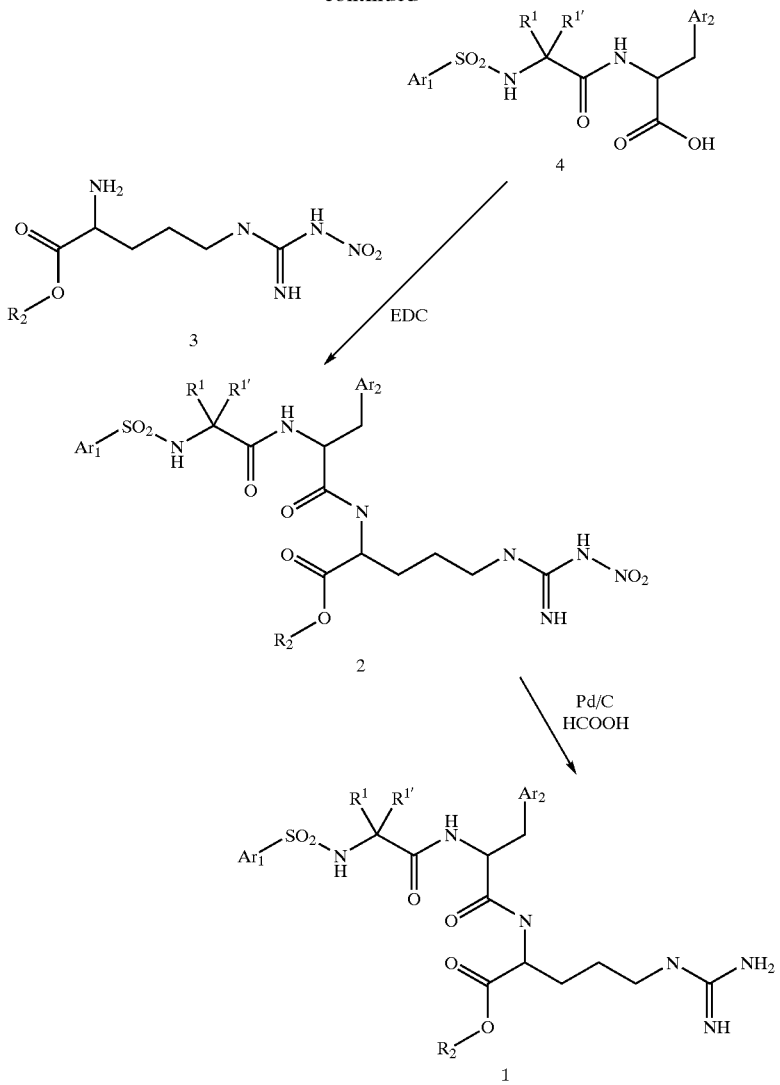

General Reaction Conditions

Generally speaking, the compounds of the present invention are made by a series of "condensation" reactions in which certain reactive groups are appropriately protected, and the sequence of condensation is controlled. Schemes I and II demonstrate that the component materials may be coupled in more than one sequence. Referring to Scheme I, the compounds of formula 1 which include an L-arginine moiety, may be prepared from the compounds of formula 2 by removal of the guanidine-protecting nitro group via a reduction reaction using formic acid as reducing agent in the presence of palladium on carbon. In a typical procedure, the reaction mixture is stirred overnight under nitrogen, filtered, and the solvent then removed under reduced pressure. Recovered material may then be triturated with diethylether, and dried overnight under high vacuum to yield the final product. Although nitro is the preferred protecting group, Boc may also be used, in which case suitable reaction conditions for deprotection are stirring with trifluoracetic acid or hydrochloric acid.

Again referring to Scheme I, the compounds of formula 2 may be prepared by condensation of the compounds of formulas 3 and 4, for example in the presence of 1,3-dimethylaminopropyl-3-ethylcarbodiimide hydrochloride hydroxybenzotriazole and dimethylaminopyridine. The reaction mixture may then be washed successively with portions of 10% aqueous hydrochloric acid solution, followed by washes with 50% saturated sodium bicarbonate solution, and saturated brine. The resulting product 2 may then be dried over anhydrous magnesium sulfate, filtered, and the solvent removed under reduced pressure.

In a preferred example of the invention, compounds of formulas 3 and 4 include amino acid moieties which confer peptide-like structure on the final product compounds, consistent with their activity as somatostain analogs. Compound 3 may represent one of several suitably protected amino acids, for example, comprising a lysine, arginine, histidine, or ornithine residue, wherein the carboxyl group thereof is protected, for example, by a suitable alkyl group ($R_2$). The stereospecificity at the subregion of the product compound defined as "W" herein is determined by the stereospecificity of the participating amino acid. In the practice of the invention, stereospecificity corresponding to an L-amino acid is preferred.

Note that L-lysine is preferably selected to provide the "W" component, when Trp derivatives (whether L or R) are used to provide the "Z" component.

L-arginine is preferably selected to provide the "W" component when Phe (or derivatives thereof such as 3-fluorophenylalaninyl- or diphenylalaninyl-) is used to provide the "Z" component. In this case, the stereochemistry provided within Phe, or a derrivative thereof, should correspond to that of L-amino acids, if possible.

The deprotection that occurs in step 2→1 can be accomplished with a different agent, for example TFA, or depending on the amino acid moiety contributed by compound 3, a different deprotection strategy can be employed. For example in the case where the amino acid moiety is lysine, or a lysine-like structure, protection of the alkylamine side chain may be accomplished by providing compound 3 as a BOC derivative,

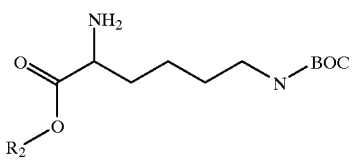

with subsequent coupling, followed by hydrolysis in HCl.

Compounds 4 are readily prepared from compounds 5 by hydrolysis under alkaline conditions, most preferably using LiOH in methanol/water.

Compounds 5 are prepared by reaction to form an amide linkage between compounds 6 and 7. It will be seen that compound 5 contributes the Z subregion of the final product 1, and is responsible for its stereospecificity. Although group $Ar_2$ therein may be any $(C_6-C_{10})$aryl group or $(C_1-C_9)$ heteroaryl group as those terms are defined in the Specification, it is again preferred that $Ar_2$ permit the Z subregion to contribute an amino acid moiety, for example, a tryptophanyl, histidinyl, phenylalaninyl or tyrosinyl group. In the practice of the invention, stereospecificity corresponding to an L-amino acid is preferred, although use of D-trypophanyl is also preferred.

Numerous recognized procedures can be used to react compounds 6 and 7 as herein required. For example, an alkyl ester of compound 6 can be reacted with a compound of formula 7 in triethylamine/methylene chloride with overnight stirring with a dehydrating agent such as dicyclohexylcarbodiimide, or more preferably, with hydroxybenzotriazole, 4-dimethylaminopyridine, and 1,3-dimethylaminopropyl-3-ethylcarbodiimide hydrochloride in methylene chloride. The solution may then be washed sequentially with sufficient portions of 10% hydrochloric acid, 50% saturated sodium bicarbonate, and saturated brine. The product may then be dried over anhydrous magnesium sulfate, filtered, and the solvent removed, for example.

It will be appreciated that groups $R^1$, $R^{1'}$ and $Ar_1$ (and the reactants that provide them) are selected to permit all of the product compounds of the invention. In this regard, the following structures are representative of those that may be used in place of compound 7 in the practice of the invention, so the moieties [A—G] in the compounds of formula (I) are defined.

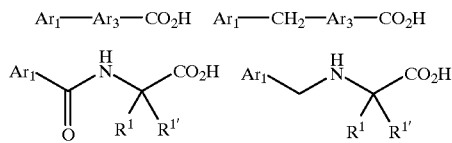

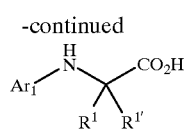

wherein $Ar_1$ (or $Ar_3$) is any $(C_6-C_{10})$aryl or $(C_1-C_9)$ heteroaryl group, and the synthesis of the resultant reactants will be apparent to those skilled in the art. For example, the above structures can be made from the corresponding amino acids.

As aforementioned, since the general reaction scheme herein involves a series of "condensations", it will be appreciated that the illustrated reactions may be conducted in a different sequence, or equivalent reaction steps can be substituted. Scheme II is one such additional possibility, and illustrations of its use are found in the numbered Examples which follow.

Schemes III(a) and III(b) provide approaches to group "W" in the general structure A—G—Z—W, where W is alternative (b)

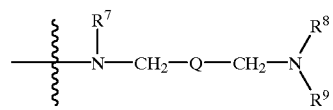

wherein
  Q is selected from the group consisting of $(C_6-C_{10})$aryl, $(C_1-C_9)$heteroaryl, $(C_3-C_{10})$cycloalkyl, and $(C_3-C_{10})$ heterocycloalkyl; and
  $R^7$, $R^8$, and $R^9$ are each independently selected from H, $(C_1-C_8)$alkyl-, and phenyl$(CH_2)$—, wherein said alkyl and phenyl groups are optionally substituted.

Schemes III(a) and III(b) outline representative syntheses of component W wherein each of $R^7$, $R^8$ and $R^9$ is H, and Q is, for example, either cyclohexane or pyridine. Numerous equivalent schemes are available to the practitioner.

Referring first to Scheme I, product 14 of Scheme III(a), and similar compounds, can replace compounds of the formula 3, so that compound analogous to compounds 2 are prepared from compounds of formula 4. Compounds analogous to those of formula 1 are then prepared from compounds of analogous to those of formula 2 by removal of the protecting BOC group under acidic conditions.

Referring to Scheme III(a), compounds of formula 14 may be prepared from compounds of 15 by reduction with hydrogen under appropriate conditions. Compounds of formula 15 may be prepared from compounds of formula 16 via reaction using $NaN_3$ to displace the mesylate ester of compounds 16. Compounds 16 may be prepared from compounds 17 with mesyl (methanesulfonyl) chloride under basic conditions, for example, in triethylamine/ dichloromethane at 0° C., in good yield. Compounds 17 may be prepared from compounds 18 by reduction at the carboxyl group thereof using $BH_3$. Compounds 18, having the stereospecificity indicated in Scheme II(a), are prepared from racemic compounds 20 by chiral resolution with stereospecific α-methylbenzylamine, followed by selective purification, such as by crystallization. Compounds 20 may be prepared from the corresponding aromatic compounds 21 by reduction with hydrogen, for example, under appropriate conditions. Compounds 21 in turn are prepared from the corresponding (unprotected) compounds 22 by reaction with BOC anhydride under standard conditions. Finally, compounds 22 may be prepared from available starting materials 23, by reduction of the cyano group with hydrogen over a Raney nickel preparation.

In Scheme III(b), advantage is taken of available starting materials to generate compounds of the formula 14' in 2 steps, first from compounds of formula 24 using BOC anhydride. Compounds 24 are generated from compounds of formula 25 by reduction of both cyano groups, again with hydrogen and Raney nickel as catalyst.

Scheme II

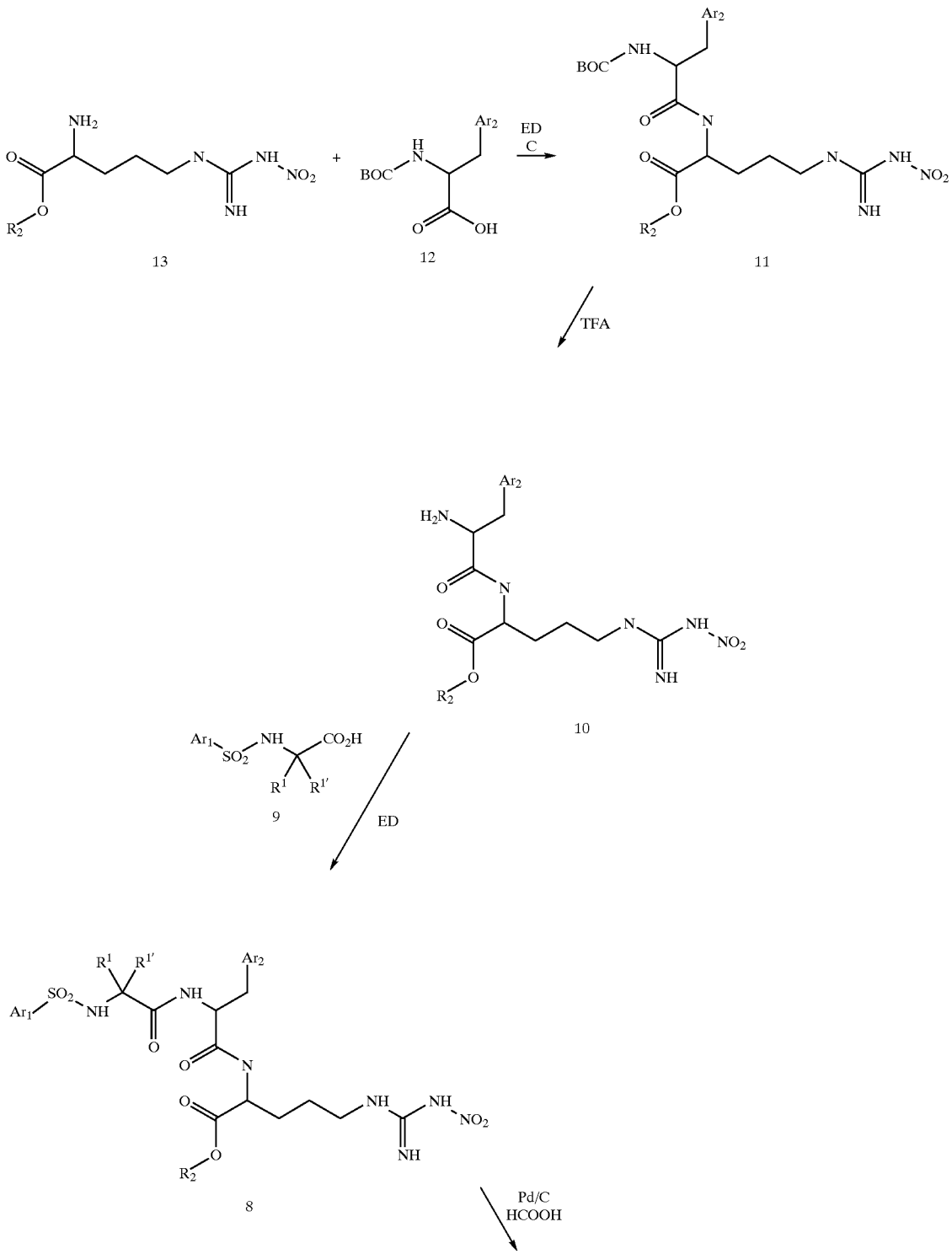

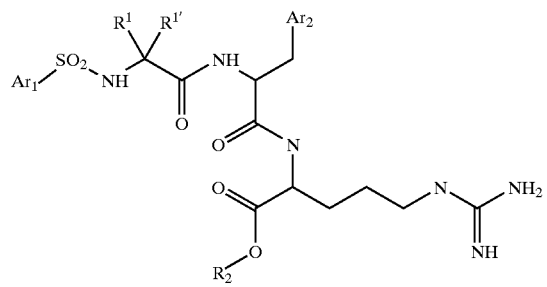
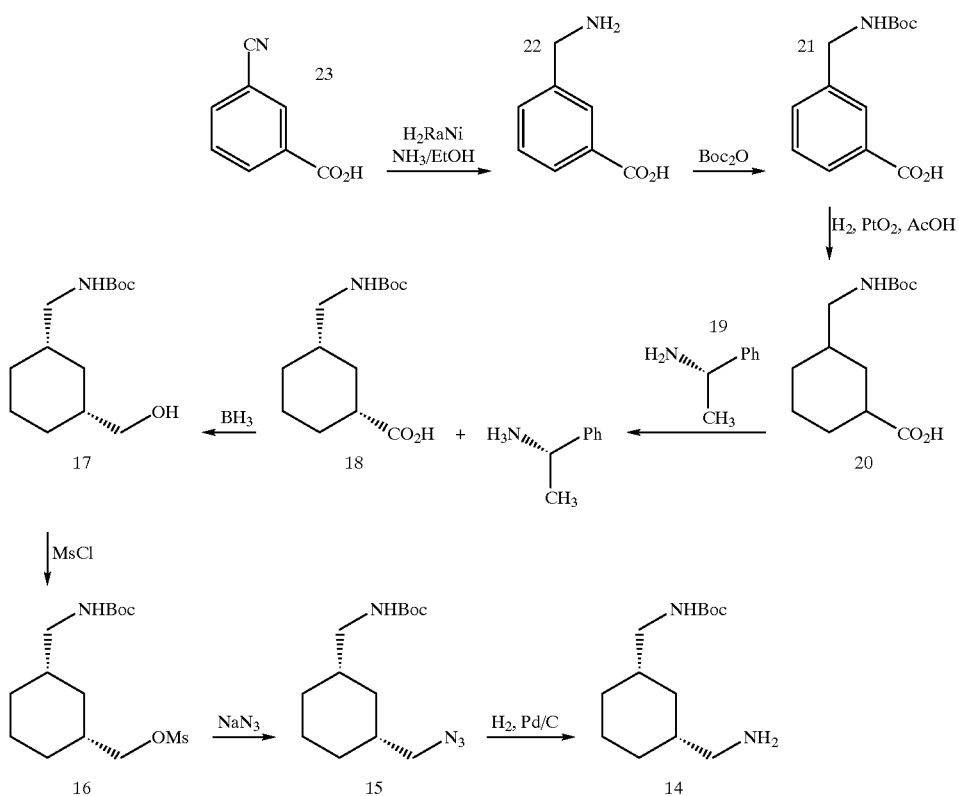
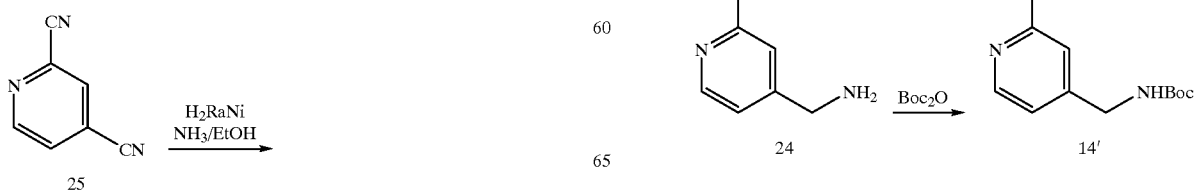

EXAMPLES

The following are representative compounds of the invention

Example 1

6-Amino-2-[2-[(biphenyl-4-ylmethyl)-amino]-3-(1H-indol-3-yl)-propionylamino]-hexanoic Acid Methyl Ester, Having the Indicated Stereospecificity.

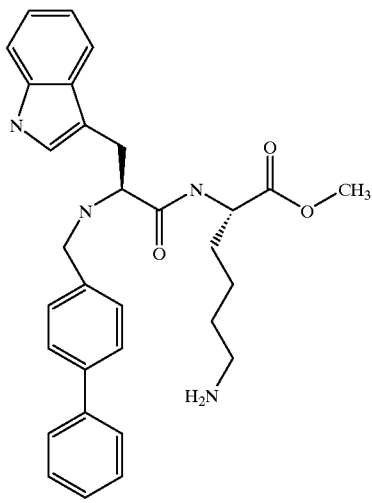

Step 1

Wang resin (Arogel Wang, Argonaut Technologies, 170 mg, 0.39 mmol/g. 0.066 mmol) was allowed to swell in 3 mL $CH_2Cl_2$ for 15 min, and washed 3X (3 times) with 3 mL $CH_2Cl_2$. A solution of Fmoc-Lsy(Boc)-OH (128 mg, 0.26 mmol), DIC (38 uL, o.26 mmol), TEA (70 uL, 0.5 mmol) and DMAP (3 mg, 0.026 mmol) in 2.5 mL $CH_2Cl_2$ was added, and the mixture was agitated by rotation for 1.5 h. The resin was then washed, consecutively, 3X with 3 mL $CH_2Cl_2$, 2X with 3 mL DMF, 2X with 3 mL EtOH, and finally 3X with 3 mL $CH_2Cl_2$. 3 mL of a 20% solution of piperidine in $CH_2Cl_2$ was then added, and the composition was agitated by rotation for 1 h. The resin was then washed, consecutively, 3X with 3 mL $CH_2Cl_2$, 2X with 3 mL DMF, 2X with 3 mL EtOH, and 3X with 3 mL $CH_2Cl_2$. A solution of Fmoc-d-Trp-OH (110 mg, 0.26 mmol), ), DIC (38 uL, 0.26 mmol), TEA (70 uL, 0.5 mmol) and DMAP (3 mg, 0.026 mmol) in 2.5 mL $CH_2Cl_2$ was then added, and the mixture was agitated by rotation for 1.5 h. The resin was next washed, consecutively, 3X with 3 mL $CH_2Cl_2$, 2X with 3 mL DMF, 2X with 3 mL EtOH, and then 3X with 3 mL $CH_2Cl_2$. 3 mL of a 20% solution of piperidine in $CH_2Cl_2$ was then added, and the mixture was agitated by rotation for 1 h. The resin was next washed, consecutively, 3X with 3 mL $CH_2Cl_2$, 2X with 3 mL DMF, 2X with 3 mL EtOH, and then 3X with 3 mL toluene.

Step 2 Preparation of the Title Compound 2.5 mL of 10% THF in toluene was added to the resin, followed by biphenyl carboxaldehyde (50 mg). The composition was agitated by rotation for 1 hour, after which 0.5 mL 1M $NaCHBH_4$ (in THF) was added, and rotation continued for 2 h. The resin was then washed, consecutively, 3X with 3 mL $CH_2Cl_2$, 2X with 3 mL DMF, 2X with 3 mL EtOH, and 3X with 3 mL of $CH_2Cl_2$. The composition was then subject to blow drying under $N_2$, and then transfered to a 4 dram vial. 3 mL of 9:1:1 MeOH, DMF, TEA solution was added, and the compostion mixed on an orbital shaker at 50 C for 2.5 days. The resin was then filtered and washed, 2X with 3 mL $CH_2Cl_2$, followed 3X with 3 mL EtOH. The resulting solid was evaporated and passed through an $SiO_2$ plug with EtOAc to deliver 10 mg product. The product was then dissolved into 2 mL 20% conc. HCl in EtOH, and then stirred at room temperature for 30 min. The resulting HCl salt was evaporated and tritrated with ether to afford 9 mg product. MS/+: 613.2; 1H NMR: 7.10 (m, 2H), 4.21 (m, 1H), 3.62 (s, 3H), 1.83 (m, 2H).

It should be noted that if the L-lysinyl residue in the backbone of the exemplified compound is replaced with a residue provided by 2,4-diaminobutyric acid, the compound was substantially less active in assays. However, replacement by L-ornithinyl- resulted in active compounds.

Example 2

2-{3-(3-Fluoro-phenyl)-2-[2-(toluene-4-sulfonylamino)-acetylamino]-propionylamino}-5-guanidino-pentanoic Acid Methyl Ester, Having the Indicated Stereospecificity.

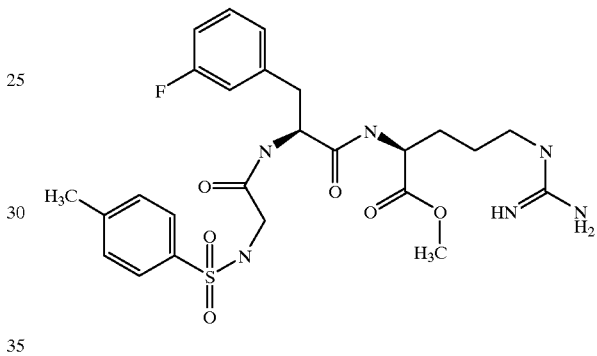

Step 1 Preparation of 3-F-Phe-Arg($NO_2$)-OMe

To a solution of 2.00 gm of BOC-3-F-Phe-OH (7.06 mmol), 2.09 gm of Arg($NO_2$)-OMe HCl (7.77 mmol), 1.05 gm of hydroxybenzotriazole and 2.58 gm of 4-dimethylaminopyridine in 50 mL of methylene chloride was added 1.5 gm of 1,3-dimethylaminopropyl-3-ethylcarbodiimide hydrochloride. After stirring for 15 hours 100 mL more methylene chloride was added to the reaction, and it was washed three times with 100 mL portions of 10% aqueous hydrochloric acid solution, twice with 100 mL of 50% saturated sodium bicarbonate solution, once with 100 mL of saturated brine, dried over anhydrous magnesium sulfate, filtered, and the solvent removed under reduced pressure to yield 2.96 gm of product. This was dissolved in 100 mL of 10% trifluoroacetic acid in methylene chloride, stirred for 2 hours, and the solvent removed rapidly under reduced pressure. The material was triturated with diethyl ether and dried under high vacuum to yield product.

Step 2 Preparation of the Title Compound

To a solution of 104 mg of tosylglycine (0.456 mmol), 273 mg of 3-F-Phe-Arg($NO_2$)-OMe HCl (0.684 mmol), 93 mg of hydroxybenzotriazole (0.689 mmol) and 167 mg of 4-dimethylaminopyridine (1.37 mmol) in 20 mL of methylene chloride was added 137 mg of 1,3-dimethylaminopropyl-3-ethylcarbodiimide hydrochloride (0.684 mmol). After stirring for 15 hours 100 mL more methylene chloride was added to the reaction, and it was washed three times with 20 mL portions of 10% aqueous hydrochloric acid solution, twice with 20 mL of 50% saturated sodium bicarbonate solution, once with 20 mL of saturated brine, dried over anhydrous magnesium sulfate, filtered, and the solvent removed under reduced pressure. This material was dissolved in 60 mL of methanol, 300 mg of 10% palladium on carbon was added under nitrogen, followed by 2.5 mL of formic acid. The mixture was stirred overnight under nitrogen, filtered, the solvent removed under reduced pressure, the material triturated with diethyl ether, and dried overnight under high vacuum to yield the product. This material can also be synthesized by coupling a suitably protected arginine fragment with a suitably protected trptophan fragment, deprotecting the tryptophan amino group, condensing this material with tosylglycine, and deprotecting the arginine sidechain. $^1$H NMR (CD$_3$OD): δ 4.65 (m, 1H); 4.42 (m, 1H); 3.72 (s, 3H); 2.45 (s, 3H). MS: M+1=565

It should be noted if the glycinyl residue in the backbone of the exemplified compound is replaced with alaninyl (whether D- or L-), the compound was substantially less active in assays. However, replacement by α-methylalaninyl- resulted in active compounds. The glycinyl residue is also usefully replaced by β-alanine and γ-aminobutyric acid.

Example 3

6-Amino-2-[2-[(biphenyl-4-carbonyl)-amino]-3-(1H-indol-3-yl)-propionylamino]-hexanoic Acid Methyl Ester, Having the Indicated Stereospecificity.

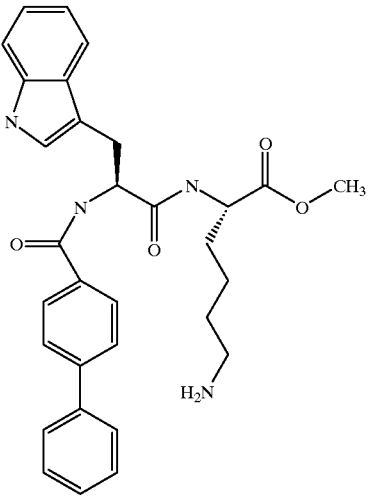

$^1$H NMR (CD$_3$OD): δ 4.32 (m, 1H); 3.39 (d, 1H); 3.63 (s, 3H); 2.87 (m, 2H). MS: M+1=527

Example 4

2-{2-[(Biphenyl-4-carbonyl)-amino]-3,3-diphenyl-propionylamino}-5-guanidino-pentanoic acid methyl ester, having the indicated stereospecificity.

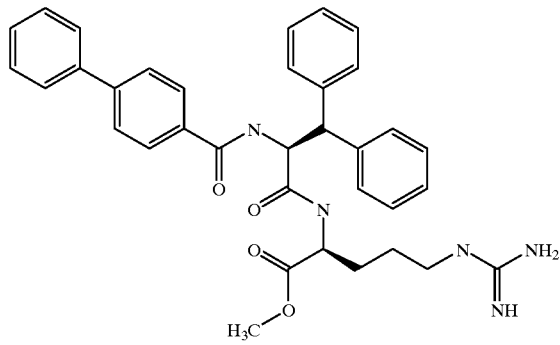

$^1$H NMR (CD$_3$OD): δ 5.45 (d, 1H); 4.55 (d, 1H); 4.25 (m, 2H); 3.49 (s, 3H). MS: M+1=592

Example 5

6-Amino-2-[2-[(biphenyl-4-carbonyl)-amino]-3-(1H-indol-3-yl)-propionylamino]-hexanoic acid tert-butyl ester, having the indicated stereospecificity.

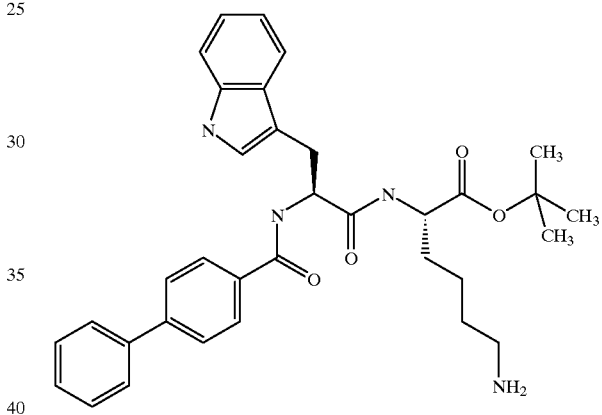

Step 1 Preparation of L-Trp-OMe 4-Biphenylcarbonylamide

Dissolve 3.45 gm (13.54 mmol) of L-Trp-Ome hydrochloride and 4.11 gm (40.6 mmol) triethylamine in 500 mL of methylene chloride. Then add 2.934 gm (13.54 mmol) of 4-biphenycarbonylchloride portionwise, and allow the reaction to stir overnight. The solution was then washed twice with 100 mL portions of 10% hydrochloric acid, twice with 100 mL portions of 50% saturated sodium bicarbonate, once with 100 mL of saturated brine, dried over anhydrous magnesium sulfate, filtered, and the solvent removed under reduced pressure to yield 4.83 gm (90%) of product.

Step 2 Preparation of L-Trp-OH 4-Biphenylcarbonylamide

L-Trp-Ome 4-Biphenylcarbonylamide (4.83 gm, 12.12 mmole) was dissolved in 120 mL of methanol, then 2.543 gm (60.6 mmol) lithium hydroxide monohydrate in 40 mL of water was added. The reaction was heated to 70 C to dissolve all of the contents, and after maintaining stirring at that temperature for 30 minutes the reaction was cooled to room temperature. The methanol was removed by rotary evaporation, and the aqueous slurry was acidified to pH 2.0 with 10% aqueous hydrochloric acid. The solid was then filtered and dried overnight under vacuum to yield 3.79 gm (81%) of product.

Step 3 Preparation of Title Compound as Trifluoroacetate Salt

To a solution of 100 mg of L-Trp-OH 4-Biphenylcarbonylamide (0.26 mmol), 132 mg of Lys(Z)-OtBu HCl (0.39 mmol), 53 mg of hydroxybenzotriazole (0.39 mmol) and 191 mg of 4-dimethylaminopyridine (1.56 mmol) in 40 mL of methylene chloride was added 150 mg (0.78 mmol) of 1,3-dimethylaminopropyl-3-ethylcarbodiimide hydrochloride. After stirring for 15 hours 100 mL more methylene chloride was added to the reaction, and it was washed three times with 30 mL portions of 10% aqueous hydrochloric acid solution, twice with 20 mL of 50% saturated sodium bicarbonate solution, once with 20 mL of saturated brine, dried over anhydrous magnesium sulfate, filtered, and the solvent removed under reduced pressure. The product was then dissolved in 10 mL of methylene chloride, 1 mL of triflouroacetic acid was added, and the reaction stirred for 3.5 hours. The solvent was then removed rapidly under reduced pressure, the product was triturated with diethyl ether, and dried under high vacuum overnight to yield 67 mg of product. This material can also be synthesized by coupling a suitably protected lysine fragment with a suitably protected tryptophan fragment, deprotecting the tryptophan amino group, condensing this material with biphenylcarbonyl chloride, and deprotecting the lysine sidechain. $^1$H NMR (CD$_3$OD): δ 4.36 (m, 1H); 3.40 (m, 1H); 2.85 (m, 2H); 1.43 (s, 9H). MS: M+1=569

Example 6

6-Amino-2-[2-[(biphenyl-4-carbonyl)-amino]-3-(1H-indol-3-yl)-propionylamino]-hexanoic acid tert-butyl ester, having the indicated stereospecificity.

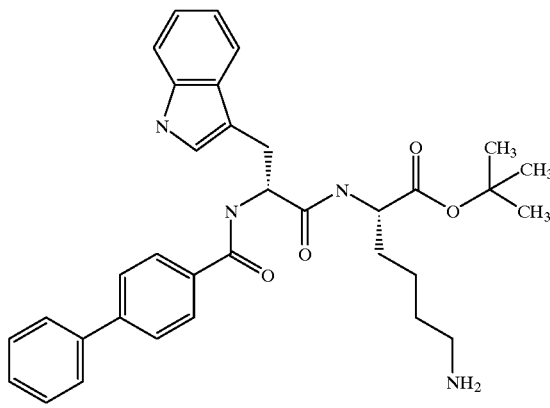

$^1$H NMR (CD$_3$OD): δ 4.18 (m, 1H); 3.45 (m, 1H); 2.78 (m, 2H); 1.40 (s, 9H). MS: M+1=569

Example 7a

6-Amino-2-[2-(2-benzenesulfonylamino-2-methyl-propionylamino)-3-(1H-indol-3-(1H-indol-3-yl)-propionylamino]-hexanoic Acid Tert-butyl Ester, Having the Indicated Stereospecificity.

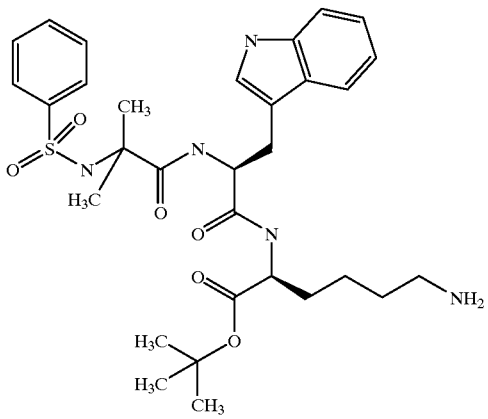

This was synthesized by coupling α-methylalaninebenzenesulfonamide (from α-methylalanine and benzenesulfonyl chloride) with (L)Trp-Ome using 1,3-dimethylaminopropyl-3-ethylcarbodiimide hydrochloride, methyl ester deprotection with LiOH, coupling with Lys(Boc)-OtBu HCl using 1,3-dimethylaminopropyl-3-ethylcarbodiimide hydrochloride, and deprotecting with trifluoroacetic acid. $^1$H NMR (CD$_3$OD): δ 4.38 (m, 1H); 4.65 (m, 1H); 3.47 (d, 2H); 1.45 (s, 6H); 1.41 (s, 9H). MS: M+1=614.

Example 7b

6-Amino-2-[2-(2-benzenesulfonylamino-2-methyl-propionylamino)-3-(1H-indol-3-yl)-propionylamino]-hexanoic acid tert-butyl ester, having the indicated stereospecificity.

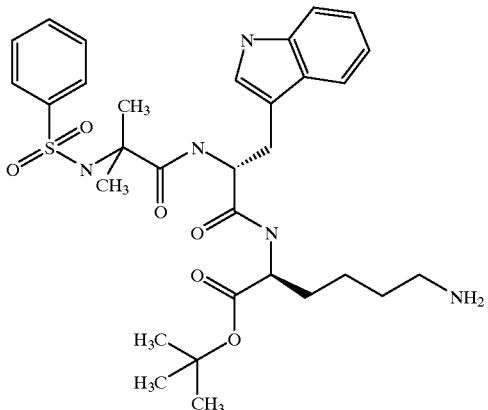

Synthetic details are as in Example 7a, except for use of (D)Trp-Ome.

Example 8

6-Amino-2-[2-{[4-(benzenesulfonylamino-methyl)-cyclohexanecarbonyl]-amino}-3-(1H-indol-3-yl)-propionylamino]-hexanoic Acid Tert-butyl Ester.

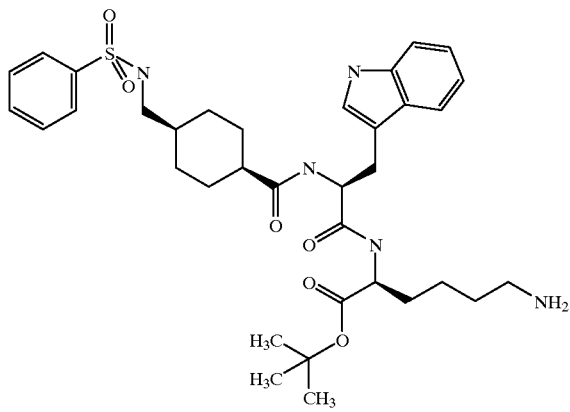

MS M+1=668.9.

The ability of compounds of formula (I), and the pharmaceutically acceptable salt, solvates or hydrate thereof (hereinafter referred to as the compounds of the present invention) to act as somatostatin antagonists, or agonists, and consequently to demonstrate their effectiveness in the treatment of disease states, is shown by the following assays.

Biological Assays

Various types of somatostain agonists are well known in the art, and the capacity of a compound of the present invention to act as an agonist, an antagonist, or as either, depending on physiological circumstances, can be predicted from the assays which are known in the art and/or described below. For example, measurement of cyclic-AMP, growth hormone release, microphysiometry responses, cell proliferation or protein kinase activity can be measured in cultured pituitary cells, cell lines or other cells such as neuroblastoma cells that express somatostatin receptors, and cells transfected with recombinant somatostatin receptors including transfected yeast cells. (Y. C. Patel et al., *Biochemical & Biophysical Research Communications*, 198(2), pp. 605–612, 1994; M. G. Cattaneo et al., *FEBS Letters*, 397 (2–3), pp. 164–168, 1996; J. A. Koenig et al., *British Journal of Pharmacology*, 120(1), pp. 45–51, 1997; D. Djordjijevic et al., *Endocrinology*, 139(5), pp. 2272–2277, 1998; W. R. Baumbach et al., *Molecular Pharmacology*, 54(5), pp. 864–73, 1998).

Generally, somatostatin or agonists thereof demonstrate inhibitory activity, hence a stimulus is first applied (e.g. forskolin for cyclic-AMP) and the inhibitory effect of somatostatin observed. Antagonists reverse the inhibitory effects of somatostatin.

The ability of compounds of formula (I), and the pharmaceutically acceptable salt, solvates or hydrate thereof (hereinafter referred to as the compounds of the present invention) to act as somatostatin antagonists, or agonists, and consequently to demonstrate their effectiveness in the treatment of disease states, is shown by the following assays.

Example 9

Bovine ("b")sst2 Binding Assay

The present example describes an assay for binding of pharmaceutically useful somatostatin agonists and antagonists at the bovine sst2 receptor.

The methods for culturing Neuro2A cells and measuring competitive binding potency ($IC_{50}$) were similar to those described by J. A. Koenig et al., "Somatostatin receptors in Neuro2A neuroblastoma cells: operational characteristics", *British J. Pharmacol.*, 120, 45–51, 1997, with the following modifications.

Binding assays were conducted 72 hours after transiently transfecting the Neuro2A cells with a plasmid (PCI-bsst2) containing an insert coding for the bovine sst2 receptor, placed downstream of the cytomegalovirus promoter. In the transfection step, $6.5 \times 10^6$ Neuro2A cells were added in 35 ml of media to each tissue culture flask (162 $cm^2$ surface area). The next day, transfection was conducted using Fugene 6 (Boehringer Mannheim, 1 814 443) according to the manufacturer's directions. The Fugene 6 (30 µl/flask) was equilibrated with 8 µg of PCI-bsst2 plasmid, and added to the Neuro2A cells in the absence of fetal bovine serum. After 3 hours, fresh serum-containing media was added. The assay buffer was modified to contain 50 mM HEPES, 5 mM $MgCl_2$, 1 mg/ml bovine serum albumin (BSA), 0.02 mg/ml bacitracin, and 10 µM each of aprotinin, leupeptin and AEBSF. The transfected Neuro2A cells were dissociated in the absence of trypsin/EDTA, in ice cold assay buffer (5.5 ml/flask), and cells were homogenized in a 55 ml Wheaton Dounce homogenizer (15–20 strokes). Membrane preparations were stored in aliquots at −70° C. Competitive binding assays and separation of bound from free radioactivity were conducted in polyethyleneimine-soaked Millipore 96 Well GF/C Filterplates, (MAFC NOB10). An amount of membrane was used that bound approximately 20% of [$^{125}$I]-somatostatin 14 tracer (Amersham, IM161), which was added to all wells at 15,000 cpm/well (approximately 15 nCi/well). Somatostatin was included in each experiment as positive control, at 7 concentrations from 0.0042 to 1.667 nM, and test compounds were included at 7 concentrations from 33 nM to 13.33 µM. The reaction volume was 300 µl and the incubation was conducted for 1 hour at 37° C. Non-specific binding was defined using 0.83 µM somatostatin 14. The incubation was terminated by vacuum filtration through the glass fiber plate bottom, followed with a 250 µl wash with assay buffer minus BSA and protease inhibitors. The plate bottom was then sealed, scintillation fluid was added (Wallac Supermix, 250 µl/well), and radioactivity was measured in a 96 well microtiter liquid scintillation counter.

$IC_{50}$ values are determined by polynomial regression and analzyed using a MACRO program. An $IC_{50}$ value of less than about 5 µM is preferred.

Example 10

Rat Pituitary Assay for Somatostatin Receptor Antagonists

This assay is designed to quantitate the activity of antagonists of somatostatin that interact directly at the somatostatin receptor. The assay facilitates discovery of agents which increase growth hormone secretion by modulating the inhibitory effects of somatostatin. As aforementioned, somatostatin (also abbreviated SRIF) inhibits GH secretion in the anterior pituitary by binding to a high affinity membrane-bound (and G-protein coupled) receptor which is coupled negatively to adenyl cyclase, thereby reducing intracellular levels of cAMP that would otherwise facilitate, for example, secretion/release of GH from cytoplasmic granules. Vasoactive intestinal peptide (VIP) is one of several endogenous peptides that stimulates GH secretion by binding to a high affinity membrane-bound receptor coupled to a G protein-dependent signal transduction pathway. VIP activates adenylate cyclase and produces increased intracellular cAMP levels. These peptides may be involved in the coordinate regulation of GH secretion under physiologic conditions and be mediated through cAMP. The cell line used in the screen is a clonal pituitary cell that synthesizes and secretes GH in response to VIP and SRIF, and many other regulatory hormones, as expected for normal pituitary cells. The screen is designed to quantitate the ability of test agents to reverse SRIF's inhibition of the elevated intracellular cAMP levels produced by VIP.

In particular, cyclic AMP (cAMP) content of the pituitary cell line $GH_4C_1$ was used to differentiate somatostatin agonists from antagonists. The method was similar to that described by L. J. Dorflinger et al. ("Somatostatin inhibits vasoactive intestinal peptide-stimulated cyclic adenosine monophosphate accumulation in GH pituitary cells", *Endocrinology*, 113, pp. 1541–50, 1983) with the following modifications. Aliquots (50 μl) of $GH_4C_1$ cell suspension at 1–2 million cells/ml were added to 50 μl of each solution of test compound in Adenylyl Cyclase Activation FlashPlate® Assay plates from NEN™ Life Science Products (catalog SMP004A). Putative somatostatin agonists or antagonists were typically tested at concentrations of 10, 1 and 0.1 μM, in the presence of 100 nM vasoactive intestinal peptide (VIP; Sigma V3628) and 10 nM somatostatin 14 (cell culture tested, Sigma S1763). The FlashPlates®, which are coated with antibody against cAMP and contain scintillant integral to the plastic, are supplied as part of a kit with all necessary reagents to estimate cAMP content of whole cell preparations, including Stimulation Buffer, Detection Buffer, cAMP Standard, and [$^{125}$I]-cAMP Tracer. This afforded a convenient way to conduct a homogenous immunoradiometric assay of cAMP content in cells lysed in situ, following incubation of the cells with test compound. cAMP content in the $GH_4C_1$ cells was determined according to the manufacturer's instructions, by comparison with standards at concentrations from 10 to 1,000 nM cAMP. In this assay, VIP increased cAMP content of the $GH_4C_1$ cells, and somatostatin caused a partial inhibition. Test compounds acting as somatostatin antagonists were detected by their tendancy to increase cAMP content in comparison to control wells containing VIP and somatostatin but no test compound. Somatostatin agonists conversely decreased cAMP content.

$IC_{50}$ values are determined by polynomial regression and analzyed using a MACRO program. An $IC_{50}$ value of less than about 5 μM is preferred.

Example 11

Effect of a Somatostatin Antagonist on GH Release in 12 kg Pigs

Studies indicate that concentrations of GH increase in small pigs within 10 minutes of administration of somatostatin antagonists, and then return to pre-treatment levels within 40 minutes post-administration.

The following protocol describes the effects of various doses of a somatostatin antagonist on release of endogenous porcine GH (or pST, porcine somatatrophin). Methods used to evaluate effects of compounds on plasma GH concentrations in barrows (castrated male pigs) were similar to those reported by M. J. Estienne et al., "Methyl-D,L-aspartate-induced growth hormone secretion in barrows: possible mechanisms of action", *Journal of Animal Science* 74, pp. 597–602, 1996, with the following modifications. Forty cross-bred barrows weighing approximately 12 kg were acclimatized for 2 days at 10 pigs per 36 sq. ft. pen, 4 pens per study, with feed (PS-9 swine starter diet) and water provided ad libitum. To enhance uniformity, two pigs/pen were eliminated based on being smallest or largest, or for health reasons, bringing the group size to 8 pigs/treatment. An equal number of pigs in each pen received 1 of 4 possible treatments at random, i.e. one of 3 doses of test compound or diluent alone. Compounds diluted in approximately 1 ml/pig sterile saline were administered by intramuscular injection into the rear leg (ham), about 1 minute after collection of the first blood sample into 7 ml heparinized evacuated tubes via jugular venepuncture. Blood samples were similarly collected at 10 minute intervals up to 40 minutes after injection of test compound or diluent. Plasma was separated by centrifugation and frozen at −20° C.).

Example 12

RIA Procedure for Determination of GH Levels in Plasma.

The present assay is used to determine GH levels (for example, porcine GH or canine GH) in plasma samples.

The double antibody radioimmunoassay (RIA) used to determine porcine GH concentrations in plasma samples was similar to that described by Y. N. Sinha et al., "Studies of GH secretion in mice by a homologous radioimmunoassay for mouse GH", *Endocrinology*, 91, pp.784–92, 1972, and that of F. Cocola et al., "A rapid radioimmunoassay method of growth hormone in dog plasma", *Proceedings of the Society for Experimental Biology and Medicine*, 151, pp. 140–14, 1976. Modifications were as follows. Native porcine GH (pGH) for radioiodination as tracer, canine GH for use as standard (cGH; AFP-1983B; the aminoacid sequence of canine and porcine GH are the same), and primary antibody (monkey anti-cGH; AFP-21452) were supplied by A. F. Parlow, Harbor UCLA Medical Center. Recombinant porcine GH from Biogenesis was alternatively used for radioiodination as tracer. Radioiodinations were conducted by Biomedical Technologies Inc, Stoughton, Mass. Primary antibody (1:50,000 or 1:100,000 final dilution), normal monkey serum (ICN 55988; 1:1,000 final dilution), and plasma sample or standard (0.08 to 2.5 ng cGH/tube) were mixed and incubated for 2 hours at ambient temperature, then tracer (10,000 cpm/tube) was added and the incubation continued for a further 20 hours at ambient temperature in a total volume of 500 μl. Secondary antibody (goat anti-monkey IgG ICN 55418; final dilution 1:160) and polyethyleneglycol 8,000 (final concentration 44 mg/ml) were added and mixed in a final volume of 1.6 ml. Tubes were incubated at 4° C. for 2 hours with shaking, then they were centrifuged, supernates discarded, and the gamma-emission of the pellets determined.

Plasma growth hormone concentrations, expressed as ng/ml, were calculated from the standard line following log-logit transformation.

What is claimed is:
1. A compound according to the formula

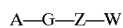

or a pharmaceutically acceptable salt, solvates or hydrate thereof, wherein

A is $(C_6-C_{10})$aryl, $(C_6-C_{10})$aryl-$SO_2$, $(C_6-C_{10})$aryl-$CH_2$—, $(C_6-C_{10})$arylcarbonyl, $(C_1-C_9)$heteroaryl, $(C_1-C_9)$heteroaryl-$SO_2$—, $(C_1-C_9)$heteroaryl-$CH_2$—; or $(C_1-C_9)$heteroarylcarbonyl;

G is:

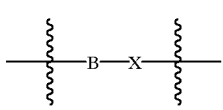

where B is $(C_6-C_{10})$aryl, and X is $CH_2$, $SO_2$, or carbonyl;

Z is

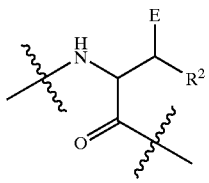

wherein $R^2$ is H, $(C_1-C_8)$alkyl, or is selected from groups A above; and E is indolyl; and W is (a):

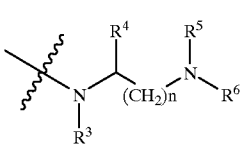

wherein n is 2–5, $R^3$ is selected from H, $(C_1-C_8)$alkyl-, and phenyl$(CH_2)$—;

$R^6$ is selected from H, $(C_1-C_8)$alkyl-, and phenyl$(CH_2)$—;

$R^4$ is selected from H, $(C_1-C_8)$alkyl-, and phenyl$(CH_2)$—, or is (1)

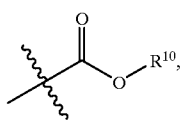

or (2)

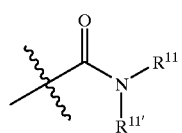

where groups $R^{10}$, $R^{11}$ and $R^{11'}$ are each, independently, selected from H, $(C_1-C_8)$alkyl-, and phenyl$(CH_2)$—;

$R^5$ is selected from H, $(C_1-C_8)$alkyl-, and phenyl$(CH_2)$—, or is

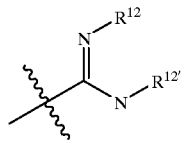

wherein $R^{12}$ and $R^{12'}$ are each independently selected from H, $(C_1-C_8)$alkyl-, and phenyl$(CH_2)$—, and wherein said $(C_6-C_{10})$aryl and $(C_1-C_9)$heteroaryl groups of A, $(C_6-C_{10})$aryl groups of B, indolyl group E, and $(C_6-C_{10})$aryl or $(C_1-C_9)$heteroaryl groups of $R^2$ are each substituted, optionally and independently, by one or more functional groups selected from hydroxy, halo, amino, trifluoromethyl, carboxy, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$acylamino-, cyano, nitro, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl$(C_1-C_6)$alkyl-, nitro$(C_1-C_6)$alkyl-, $(C_1-C_3)$alkyl (difluoromethylene)$(C_1-C_3)$alkyl-, $(C_1-C_6)$acylamino$(C_1-C_6)$alkyl, $(C_1-C_6)$alkoxy$(C_1-C_6)$acylamino-, amino$(C_1-C_6)$acyl-, amino$(C_1-C_6)$acyl$(C_1-C_6)$alkyl-, $(C_1-C_6)$alkylamino$(C_1-C_6)$acyl-, $((C_1-C_6)$alkyl$)_2$amino$(C_1-C_6)$acyl-, $(C_3-C_{10})$cycloalkyl$(C_1-C_6)$alkyl-, $(C_1-C_6)$acyloxy$(C_1-C_6)$alkyl-, $(C_2-C_6)$alkoxy$(C_1-C_6)$alkyl-, piperazinyl$(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkylsulfinyl$(C_1-C_6)$alkyl-, $(C_6-C_{10})$arylsulfinly$(C_1-C_6)$alkyl-, $(C_1-C_6)$alkysulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6)$alkyl-, $(C_1-C_6)$alkyl(difluoromethylene)-, $(C_1-C_3)$alkyl(difluoromethylene)$(C_1-C_3)$alkyl-, $(C_1-C_6)$alkoxy$(C_1-C_6)$acyl-, $(C_1-C_6)$alkylamino$(C_1-C_6)$acyl-, $((C_1-C_6)$alkyl$)_2$amino$(C_1-C_6)$acyl-, $(C_6-C_{10})$aryl-, $(C_5-C_9)$heteroaryl-, $(C_6-C_{10})$aryl$(C_1-C_6)$alkyl-, $(C_2-C_9)$heteroaryl$(C_1-C_6)$alkyl-, $(C_6-C_{10})$aryl$(C_6-C_{10})$aryl-, $(C_6-C_{10})$aryl$(C_6-C_{10})$aryl$(C_1-C_6)$alkyl-, $(C_3-C_{10})$cycloalkyl-, $(C_3-C_6)$cycloalkyl$(C_1-C_6)$alkyl-, $(C_3-C_{10})$heterocycloalkyl-, $(C_3-C_{10})$heterocycloalkyl$(C_1-C_6)$alkyl-, hydroxy$(C_2-C_6)$alkyl-, $(C_1-C_6)$acyloxy$(C_2-C_6)$alkyl-, $(C_1-C_6)$alkoxy$(C_2-C_6)$alkyl-, piperazinyl$(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkysulfinyl$(C_1-C_6)$alkyl-, $(C_6-C_{10})$arylsulfinyl$(C_1-C_6)$alkyl-, $(C_1-C_6)$alkylsulfonyl$(C_1-C_6)$alkyl-, $(C_6-C_{10})$arysulfonyl$(C_1-C_6)$alkyl-, amino$(C_{12}$.

12. The compound of claim 1, wherein, independently, one or both of groups A and B are $(C_6-C_{10})$aryl groups, selected from phenyl and naphthyl, and said one or both $(C_6-C_{10})$aryl groups are substituted, optionally and independently, by one or more functional groups selected from the hydroxy, halo, amino, trifluromethyl, carboxy, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$acylamino-, cyano, nitro, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl ($C_1$–$C_6$)alkyl-, nitro($C_1$–$C_6$)alkyl-, ($C_1$–$C_3$)alkyl(difluoromethylene)($C_1$–$C_3$)alkyl-, ($C_1$–$C_6$)acylamino($C_1$–$C_6$)alkyl-, ($C_1$–$C_6$)alkoxy($C_1$–$C_6$)acylamino-, amino($C_1$–$C_6$)acyl-, amino($C_1$–$C_6$)acyl($C_1$–$C_6$)alkyl-, ($C_1$–$C_6$)alkylamino($C_1$–$C_6$)acyl-, (($C_1$–$C_6$)alkyl)$_2$amino($C_1$–$C_6$)acyl-, ($C_3$–$C_{10}$)cycloalkyl($C_1$–$C_6$)alkyl-, ($C_1$–$C_6$)acyloxy($C_1$–$C_6$)alkyl-, ($C_2$–$C_6$)alkoxy($C_1$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_2$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkysulfinyl($C_1$–$C_6$)alkyl- ($C_6$–$C_{10}$)arysulfinyl($C_1$–$C_6$)alkyl-, ($C_1$–$C_6$)alkylsulfonyl($C_1$–$C_6$)alkyl-, ($C_6$–$C_{10}$)arysulfonyl($C_1$–$C_6$)alkyl-, amino($C_1$–$C_6$)alkyl-, ($C_1$–$C_6$)alkylamino($C_1$–$C_6$)alkyl-, ($C_1$–$C_6$)alkyl(difluoromethylene)-, ($C_1$–$C_3$)alkyl(difluoromethylene)($C_1$–$C_3$)alkyl-, ($C_1$–$C_6$)alkoxy($C_1$–$C_6$)acyl-, ($C_1$–$C_6$)alkylamino($C_1$–$C_6$)acyl-, (($C_1$–$C_6$)alkyl)$_2$amino($C_1$–$C_6$)acyl-, ($C_6$–$C_{10}$)aryl-, ($C_3$–$C_9$)heteroaryl-, ($C_6$–$C_{10}$)aryl($C_1$–$C_6$)alkyl-, ($C_2$–$C_9$)heteroaryl($C_1$–$C_6$)alkyl-, ($C_6$–$C_{10}$)aryl($C_6$–$C_{10}$)aryl-, ($C_6$–$C_{10}$)aryl($C_6$–$C_{10}$)aryl($C_1$–$C_6$)alkyl- ($C_3$–$C_{10}$)cycloalkyl-, ($C_3$–$C_6$)cycloalkyl($C_1$–$C_6$)alkyl-, ($C_3$–$C_{10}$)heterocycloalkyl-, ($C_3$–$C_{10}$)heterocycloalkyl($C_1$–$C_6$)alkyl-, hydroxy($C_2$–$C_6$)alkyl-, ($C_1$–$C_6$)acyloxy($C_2$–$C_6$)alkyl-, ($C_1$–$C_6$)alkoxy($C_2$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_2$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkysulfinyl($C_1$–$C_6$)alkyl-, ($C_6$–$C_{10}$)arysulfinyl($C_1$–$C_6$)alkyl-, ($C_1$–$C_6$)alkylsulfonyl($C_1$–$C_6$)alkyl-, ($C_6$–$C_{10}$)arysulfonyl($C_1$–$C_6$)alkyl-, amino($C_1$–$C_6$)alkyl-, ($C_1$–$C_6$)alkylamino($C_1$–$C_6$)alkyl-, and (($C_1$–$C_6$)alkyl$_2$amino($C_1$–$C_6$)alkyl.

3. The compound of claim 1, wherein group A is a ($C_1$–$C_9$)heteroaryl group selected from furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, and benzoxazinyl, and said ($C_1$–$C_9$)heteroaryl group is optionally substituted by one or more functional groups selected from hydroxy, halo, amino, trifluromethyl, carboxy, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, nitro($C_1$–$C_6$)alkyl-, ($C_1$–$C_3$)alkyl(difluoromethylene)($C_1$–$C_3$)alkyl-, ($C_1$–$C_6$)acylamino($C_1$–$C_6$)alkyl-, ($C_1$–$C_6$)alkoxy($C_1$–$C_6$)acylamino, amino($C_1$–$C_6$)acyl-, amino($C_1$–$C_6$)acyl($C_1$–$C_6$)alkyl-, ($C_1$–$C_6$)alkylamino($C_1$–$C_6$)acyl-, (($C_1$–$C_6$)$_2$amino($C_1$–$C_6$)acyl-, ($C_3$–$C_{10}$)cycloalkyl($C_1$–$C_6$)alkyl-, ($C_1$–$C_6$)acyloxy ($C_1$–$C_6$)alkyl-, ($C_2$–$C_6$)alkoxy($C_1$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_2$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkylsulfinyl($C_1$–$C_6$)alkyl- ($C_6$–$C_{10}$)arylsulfinyl($C_1$–$C_6$)alkyl, ($C_1$–$C_6$)alkylsulfonyl($C_1$–$C_6$)alkyl-, ($C_6$–$C_{10}$)arylsulfonyl($C_1$–$C_6$)alkyl-, amino ($C_1$–$C_6$)alkyl-, ($C_1$–$C_6$)alkylamino($C_1$–$C_6$)alkyl-, ($C_1$–$C_6$)alkyl(difluoromethylene)-, ($C_1$–$C_3$)alkyl(difluoromethylene)($C_1$–$C_3$)alkyl-, ($C_1$–$C_6$)alkoxy($C_1$–$C_6$)acyl-, ($C_1$–$C_6$)alkylamino($C_1$–$C_6$)acyl-, (($C_1$–$C_6$)alkyl)$_2$amino($C_1$–$C_6$)acyl-, ($C_6$–$C_{10}$)aryl-, ($C_5$–$C_9$)heteroaryl-, ($C_6$–$C_{10}$)aryl($C_1$–$C_6$)alkyl-, ($C_2$–$C_9$)heteroaryl($C_1$–$C_6$)alkyl-, ($C_6$–$C_{10}$)aryl($C_6$–$C_{10}$)aryl($C_1$–$C_6$)alkyl-($C_3$–$C_{10}$)cycloalkyl-, ($C_3$–$C_6$)cycloalkyl($C_1$–$C_6$)alkyl-, ($C_3$‘$C_{10}$)heterocycloalkyl-, ($C_3$–$C_{10}$)heterocycloalkyl($C_1$–$C_6$)alkyl-, hydroxy($C_2$–$C_6$)alkyl-, ($C_1$–$C_6$)acyloxy($C_2$–$C_6$)alkyl-, ($C_1$–$C_6$)alkoxy($C_2$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_2$–$C_9$)heteroaryl($C_1$–$C_6$)alkoxy($C_1$–$C_6$)alkyl-, ($C_1$–$C_6$)alkylthio($C_1$–$C_6$)alkyl-, ($C_1$–$C_6$)arylthio($C_1$–$C_6$)alky-, ($C_1$–$C_6$)alkysulfinyl($C_1$–$C_6$)alkyl-, ($C_6$–$C_{10}$)arysulfinyl($C_1$–$C_6$)alkyl-, ($C_1$–$C_6$)alkylsulfonyl ($C_1$–$C_6$)alkyl-, ($C_6$–$C_{10}$)arysulfonyl($C_1$–$C_6$)alkyl-, amino ($C_1$–$C_6$)alkyl-, ($C_1$–$C_6$)alkylamino($C_1$–$C_6$)alkyl-, and (($C_1$–$C_6$)alkyl)$_2$amino($C_1$–$C_6$)alkyl.

4. A compound according to claim 1 selected from the group consisting of:

6-Amino-2-[2-[(biphenyl-4-ylmethyl)-amino]-3-(1H-indol-3-yl)-propionylamino]- hexanoic acid methyl ester;

6-Amino-2-[2-[(biphenyl-4-carbonyl)-amino]-3-(1H-indol-3-yl)-propionylamino]- hexanoic acid methyl ester; and 6-Amino-2-[2-[(biphenyl-4-carbonyl)-amino]-3-(1H-indol-3-yl)-propionylamino]- hexanoic acid tert-butyl ester.

5. A compound according to claim 4 that is

6-Amino-2-[2-[(biphenyl-4-carbonyl)-amino]-3-(1H-indol-3-yl)-propionylamino]- hexanoic acid tert-butyl ester.

6. A compound according to claim 1, wherein the Z group thereof has the stereospecificity and E is indolyl.

7. A compound according to claim 6, wherein the Z group defines an L-amino acid that is L-tryptophanyl.

8. A compound according to claim 1, wherein the Z group thereof has the stereospecificity and E is indolyl.

9. A compound according to claim 8, wherein the Z group defines a D-amino acid that is D-tryptophanyl.

10. A compound according to claim 1, wherein the W group thereof has an absolute stereospecific configuration at the indicated position which corresponds to the that of the α-carbon of L-amino acids

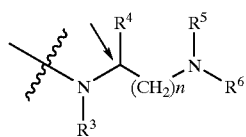

11. A compound according to claim 10, wherein the W group is an L-lysine group or a ($C_1$–$C_8$)alkyl ester thereof, an L-ornithine group or a ($C_1$–$C_8$)alkyl ester thereof, an L-arginine group or a ($C_1$–$C_8$)alkyl ester thereof.

12. A compound according to claim 11, wherein said W group is a ($C_1$–$C_8$)alkyl ester of L-lysine.

13. A compound according to claim 1 wherein $R^2$ is ($C_1$–$C_3$)alkyl-, optionally substituted by one or more halo or trifluoro($C_1$–$C_8$)alkyl groups.

14. A compound according to claim 1 wherein $R^2$ is ($C_1$–$C_8$)alkyl-, optionally substituted by one or more halo or trifluoro($C_1$–$C_8$)alkyl groups.

15. A compound according to claim 1 wherein one or more of $R^3$, $R^4$, $R^5$, and $R^6$ is ($C_1$–$C_8$)alkyl- or phenyl($CH_2$)-, and said alkyl or phenyl group is optionally substituted by one or more halo or trifluro($C_1$–$C_8$)alkyl groups.

16. A compound according to claim 1 wherein one or more of $R^{10}$, $R^{11}$, and $R^{11'}$ is ($C_1$–$C_8$)alkyl- or phenyl($CH_2$)-, and said alkyl or phenyl group is optionally substituted by one or more halo or trifluro($C_1$–$C_8$)alkyl groups.

17. A compound according to claim 1 wherein one or more of $R^{12}$ and $R^{12'}$ is ($C_1$–$C_8$)alkyl- or phenyl($CH_2$)-, and said alkyl or phenyl group is optionally substituted by one or more halo or trifluoro($C_1$–$C_8$)alkyl groups.

18. A compound according to claim 1 wherein a trifluoro ($C_1$–$C_8$)alkyl substituent present on an A, B, E, $R^2$, $R^3$, $R^4$, $R^5$, $R^6$, $R^{10}$, $R^{11}$, $R^{11'}$, $R^{12}$, $R^{12'}$ group thereof is trifluoromethyl.

19. A pharmaceutical composition for increasing secretion of gastrin, glucagon or growth hormone in a mammal, comprising an effective amount of a compound according to claim 1, and a pharmaceutical carrier.

20. A pharmaceutical composition according to claim 19 further comprising growth hormone releasing peptide (GHRP) or growth hormone releasing hormone (GHRH).

21. A compound according to claim 10, wherein the W group comprises an L-2,4-diaminobutyric or L-epsilon-N-methyllysine group, or a ($C_1$–$C_8$)alkyl ester of any thereof.

* * * * *